(12) United States Patent
Shimoda et al.

(10) Patent No.: US 9,381,223 B2
(45) Date of Patent: Jul. 5, 2016

(54) METHODS FOR INHIBITING ADVANCED GLYCATION END PRODUCT PRODUCTION, INHIBITING FIBROBLAST APOPTOSIS, AND/OR PROMOTING HUMAN FIBROBLAST-COLLAGEN GRATING FORMULATION USING CHERRY BLOSSOM AND CHERRY LEAF EXTRACT

(71) Applicant: ORYZA OIL & FAT CHEMICAL CO., LTD., Ichinomiya-shi, Aichi (JP)

(72) Inventors: Hiroshi Shimoda, Aichi (JP); Takashi Watanabe, Aichi (JP); Hiromichi Murai, Aichi (JP); Masayuki Yoshikawa, Aichi (JP)

(73) Assignee: ORYZA OIL & FAT CHEMICAL CO., LTD., Ichinomiya-shi, Aichi (JP)

( * ) Notice: Subject to any disclaimer, the term of this patent is extended or adjusted under 35 U.S.C. 154(b) by 0 days.

(21) Appl. No.: 14/225,575

(22) Filed: Mar. 26, 2014

(65) Prior Publication Data

US 2015/0174188 A1 Jun. 25, 2015

Related U.S. Application Data

(63) Continuation of application No. 13/576,433, filed as application No. PCT/JP2011/052905 on Feb. 10, 2011, now abandoned.

(30) Foreign Application Priority Data

Feb. 10, 2010 (JP) .................................. 2010-027351
Feb. 25, 2010 (JP) .................................. 2010-039465

(51) Int. Cl.

| | |
|---|---|
| A61K 36/736 | (2006.01) |
| A61K 31/7028 | (2006.01) |
| A61K 31/7032 | (2006.01) |
| A61K 31/7048 | (2006.01) |
| A61K 8/60 | (2006.01) |
| A23G 3/36 | (2006.01) |
| A23G 4/06 | (2006.01) |
| A23C 9/13 | (2006.01) |
| C07H 13/04 | (2006.01) |
| C07H 17/07 | (2006.01) |
| A61Q 19/08 | (2006.01) |
| A23L 1/30 | (2006.01) |
| A61K 8/97 | (2006.01) |
| A61K 31/7024 | (2006.01) |
| A61K 36/73 | (2006.01) |

(52) U.S. Cl.
CPC ............... *A61K 36/736* (2013.01); *A23C 9/13* (2013.01); *A23G 3/36* (2013.01); *A23G 4/06* (2013.01); *A23L 1/3002* (2013.01); *A61K 8/602* (2013.01); *A61K 8/97* (2013.01); *A61K 31/7024* (2013.01); *A61K 31/7028* (2013.01); *A61K 31/7032* (2013.01); *A61K 31/7048* (2013.01); *A61K 36/73* (2013.01); *A61Q 19/08* (2013.01); *C07H 13/04* (2013.01); *C07H 17/07* (2013.01); *A23C 2240/15* (2013.01); *A61K 2236/30* (2013.01)

(58) Field of Classification Search
CPC ............ A61K 36/736; A61K 31/7028; A61K 31/7032; A61K 31/7048; A61K 8/602
See application file for complete search history.

(56) References Cited

FOREIGN PATENT DOCUMENTS

| | | |
|---|---|---|
| JP | 08-245409 | 9/1996 |
| JP | 2000-324629 | 11/2000 |
| JP | 2002-220334 | 8/2002 |
| JP | 2003-12489 | 1/2003 |
| JP | 2004-217544 | 8/2004 |
| JP | 2005-170935 | 6/2005 |
| JP | 2005-320262 | 11/2005 |
| JP | 2005-343842 | 12/2005 |
| JP | 2006-028090 | 2/2006 |
| JP | 2007-119430 | 5/2007 |
| JP | 2009-096731 | 5/2009 |
| JP | 2009-545604 | 12/2009 |
| WO | 2009/007412 | 1/2009 |

OTHER PUBLICATIONS

Gkogkolou et al, "Advanced glycation end products", Dermatoendocrinol. Jul. 1, 2012, 4(3): 259-270).*
Toshihiro Nohara et al. "Ohi, Hana . . . ni Tsuite", The Japanese Society of Pharmacognosy Nenkai Koen Yoshishu, 2009, vol. 56, p. 191.
Yoo Nam Hee et al., Erigeroflavanone . . . Inhibitory Activity, J Nat Prod, 2008, vol. 71, No. 4, p. 713-715.
Noshita, Toshiro et al., Isolation of ethyl . . . Prunus yedoensis, Journal of Natural Medicines, 2006, 60(3), pp. 266-267.
Ostrowska, B. et al., Flavonyl glycosides . . . Padus avium, Planta Medica, 1971, 20(3), pp. 263-271.
Jang, Hyun Ah et al., in vitro . . . in Korea, Archives of Pharmacal Research, 2002, 25(6) pp. 865-872.
Oriza Yuka et al., Feb. 2, 2010, pp. 1-5, internet <URL:http://www.oryza.co.jp/pdf/sakura_news100303.pdf>.

* cited by examiner

*Primary Examiner* — Jonathan S Lau
(74) *Attorney, Agent, or Firm* — Clark & Brody

(57) ABSTRACT

Disclosed is an AGE production inhibitor or the like, which effectively inhibits the production of an advanced glycation end product (AGE), while having improved biological safety. Specifically disclosed is an AGE production inhibitor or the like, which contains en extract of cherry tree (preferably blossoms or leaves thereof) and/or a processed product of the extract as an active substance. The AGE production inhibitor or the like contains, as an active substance, at least one compound that is selected from among 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and Quercetin 3-O-(6"-malony)-β-D-glucopyranoside.

6 Claims, 8 Drawing Sheets

Normal-1

Control-1

10 mg/kg -3

50 mg/kg -1

100 mg/kg -1

TUNEL stained positive cell (▲, x 400)

METHODS FOR INHIBITING ADVANCED GLYCATION END PRODUCT PRODUCTION, INHIBITING FIBROBLAST APOPTOSIS, AND/OR PROMOTING HUMAN FIBROBLAST-COLLAGEN GRATING FORMULATION USING CHERRY BLOSSOM AND CHERRY LEAF EXTRACT

TECHNICAL FIELD

This invention relates to a new AGE production inhibitor. Regarding this invention, the AGE production inhibitor has an inhibitory effect on fibroblast apoptosis which is induced by CML-collagen (carboxymethyl lysine-collagen), an AGE, and is widely used as a material for foods, medicines, cosmetics or the like.

TECHNICAL BACKGROUND

There may still be much unknown about the production process of Advanced Glycation End-products (hereinafter referred to as AGE). However, it is thought that the key factor of AGE is a non-enzymatic glycation. In other words, it is thought that in the initial-stage reaction of AGE production, an amino group that exists in protein and an aldehyde group which is a reducing sugar such as glucose or the like, non-enzymatically react to each other (i.e. glycation), which produces Amadori-rearrangement products through Schiff's base. In the late-stage reaction, AGE is produced after a long period of complex cleavages and condensations.

Diabetes complication includes retinopathy, nephropathia, neuropathy, ischemic cardiac disease, cerebrovascular disease and others. It is known that one of the factors for the cause of these diseases relates to AGE produced in a hyperglycemic biological body. (For instance, refer to non-patent reference 1)

Diabetic nephropathy is renal microvascular damage caused by diabetes. Its basic pathological change includes the thickening of the glomerular basement membrane and the expansion of the mesangial area. Recently a number of diabetic patients stricken with the end-stage renal disease, caused by diabetic nephropathy increases and so were treated with dialysis. It is thought that AGE which is produced by a continuous state of hyperglycemia is involved in the development of nephropathy which is developed by 1. enhanced vascular permeability, 2. enhanced deposition of protein and lipoprotein, 3. inactivation of nitric oxide (NO), and 4. accelerated production of extracellular matrix. (See Non-patent Reference 2.)

For the sake of the prevention of and for the improvement of diabetic complications, various types of AGE production inhibitors have been researched and developed.

For example, it is shown that AGE production that induces diabetic complications such as nephropathia, retinopathy and others is inhibited by synthetic drugs (synthetic compounds). (See Patent References 1 and 2.) However, such synthetic drugs [that inhibit such] AGE production remains in the developmental stage, and such synthetic drugs often produce unanticipated side effects.

Contrarily, research is being done of substances or food compositions which prevent, control, improve and cure diseases through a daily dietary way of life, instead of using synthetic drugs. Patent References 3 to 5, for instance, show compositions of extracts of plants used for food, which inhibit AGE production.

However, AGE inhibitory activity of such extracts derived from plants is generally very low, compared to that of synthetic drugs (synthetic compounds), and the amount of the extracted active substance is extremely small.

To prevent or cure diabetic complications, continuous and long-term therapy is required. Thus, it is desired to develop an AGE production inhibitor that both effectively inhibits AGE production and avoids side effects. However, little is known about conventional botanical extracts which meet public expectation.

In recent years, it has been disclosed that AGE relates closely not only to diabetes but also to the aging of the skin. AGE increases with aging, and when Maillard reaction occurs in the collagen part [of the skin] which is the skin protein, the carbonyl group of glucide, non-enzymatically reacts with either the amino group of lysine residue or with the guanidyl group or arginine group in the protein to produce AGE, thus resulting in collagen cross-linking. Once the link structure is formed, the molecule is hardened, and inherent elasticity of the skin is lost. Also, such crosslink substances are treated as foreign substances, and the volume of secretion of degrading enzyme (collagenase, elastase) increases, which decreases skin tone and firmness and weakens the skin, thus resulting in wrinkles, slackness and dullness of the skin.

As such, AGE is now recognized as a trigger of diabetes complications. From the viewpoint of anti-aging care, the production mechanism of AGE is also focused.

PRIOR ARTS

Patent References (Patent Reference 1) JP-A-2000-324629
(Patent Reference 2) JP-A-2005-170935
(Patent Reference 3) JP-A-2006-28090
(Patent Reference 4) JP-A-2005-343842
(Patent Reference 5) JP-A-2005-320262

Non-Patent References (Non-patent Reference 1) Higasi, T. et. al. (Bio Clinica, Vol. 12-2, pp. 19-21, 1997)
(Non-patent Reference 2) Baba, T. et. al. (Bio Clinica, Vol. 12-2, pp. 39-48, 1997)

SUMMARY OF THE INVENTION

Problems to be Solved by the Invention

In such circumstances, the inventors conducted research on the components and amount of the components contained in the extract and of the various plant origins. They focused on "cherry tree" which contains plenty of polyphenol. After conducting various experiments, they realized that the extract of cherry blossoms and cherry leaves, especially, contain phenylpropanoid glycoside (caffeoyl glucose, coumaroyl glucose, cinnamoyl glucose) and flavonoid glycoside (kaempferol glucoside, quercetin glucoside, kaempferol malonyl glucose, quercetin malonyl glucose), which effectively inhibits AGE production and promotes the formation of fibroblast-collagen grating.

Also, the inventors learned of a new physiological activity of cherry tree extract, which effectively inhibits fibroblast apoptosis caused by an AGE, CML-collagen (i.e. Carboxymethyl Lysine-collagen), thus providing this invention.

This invention is to solve the problems, above, and its purpose is effectively to inhibit AGE production and to provide a biologically safe AGE production inhibitor for the human body.

Also, another purpose of the invention is to provide an apoptosis inhibitor to inhibit the formation of human fibroblast apoptosis caused by AGE, such as CML-collagen (Carboxymethyl lysine-collagen).

Moreover, another purpose of the invention is to provide a fibroblast collagen grating formation promoter.

Still another purpose of the invention is to provide an AGE production inhibitor effectively to inhibit AGE production within the fibroblast.

Means to Resolve the Problems

In light of resolving the above problems, the features of this invention are as follows.

1. The AGE production inhibitor of this invention contains cherry extract and/or its processed substance as an active substance.
2. The AGE production inhibitor of this invention contains cherry blossom extract and/or its processed substance as an active substance.
3. The AGE production inhibitor of this invention contains cherry leaf extract and/or its processed substance as an active substance.
4. The AGE production inhibitor of this invention contains at least one compound as an active substance selected from among 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and (Quercetin 3-O-(6"-malony)-β-D-glucopyranoside.
5. The AGE production inhibitor of this invention contains 1-O-(E)-Caffeoyl-β-D-glucopyranoside, as an active substance.
6. The AGE production inhibitor of this invention contains Quercetin 3-O-β-D-glucopyranoside as an active substance.

The AGE production inhibitor of this invention, according to the above features 1 to 6, allows the edible and safe cherry-derived extract to inhibit effectively AGE production and to avoid side effects, thus providing an ingredient for foods, medicines, cosmetics and other products which are helpful in effectively preventing or treating diabetic complications.

7. The apoptosis inhibitor of this invention contains cherry extract and/or its processed substance as an active substance, which inhibits fibroblast apoptosis caused by CML-collagen (i.e. Carboxymethyl lysine-collagen) which is an AGE.
8. The apoptosis inhibitor of this invention contains cherry blossom extract and/or its processed substance as an active substance, which inhibits fibroblast apoptosis caused by CML-collagen (i.e. Carboxymethyl lysine-collagen) which is an AGE.
9. The apoptosis inhibitor of this invention contains cherry leaf extract and/or its processed substance as an active substance, which inhibits fibroblast apoptosis caused by CML-collagen (i.e. Carboxymethyl lysine-collagen) which is an AGE.
10. The apoptosis inhibitor of this invention contains at least one active substance selected from among 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside and Quercetin 3-O-(6"-malony)-β-D-glucopyranoside, which inhibits the fibroblast apoptosis caused by the CML-collagen (i.e. Carboxymethyl lysine-collagen) which is an AGE.
11. The apoptosis inhibitor of this invention contains 1-O-(E)-Caffeoyl-β-D-glucopyranoside as an active substance, which inhibits fibroblast apoptosis caused by CML-collagen (i.e. Carboxymethyl lysine-collagen) which is an AGE.
12. The apoptosis inhibitor of this invention contains Quercetin 3-O-β-D-glucopyranoside and/or Quercetin 3-O-(6"-malony)-β-D-glucopyranoside as an active substance, which inhibits fibroblast apoptosis caused by CML-collagen (i.e. Carboxymethyl lysine-collagen) which is an AGE.

The AGE production inhibitor of this invention, according to the above features 7 to 12, allows cherry-derived extract, which is safe for food, to inhibit effectively the fibroblast apoptosis caused by CML-collagen (Carboxymethyl lysine-collagen), thus providing a material for foods, medicines, cosmetics and other products, which is helpful in effectively preventing or inhibiting the skin from aging.

13. The human fibroblast-collagen grating-formation promoter of this invention contains cherry-tree extract and/or its processed substance as an active substance.
14. The human fibroblast-collagen grating-formation promoter of this invention contains cherry-blossom extract and/or its processed substance as an active substance.
15. The human fibroblast-collagen grating-formation promoter of this invention contains cherry-leaf extract and/or its processed substance as an active substance.
16. The human fibroblast-collagen grating-formation promoter of this invention contains at least one active substance selected from among this group of compounds: 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-β-D-glucopyranoside, Kaempferol 3-O-(6"-malony)-β-D-glucopyranoside and Quercetin 3-O-(6"-malony)-β-D-glucopyranoside.
17. The human fibroblast-collagen grating-formation promoter of this invention contains 1-O-(E)-Caffeoyl-β-D-glucopyranoside as an active substance.
18. The human fibroblast-collagen grating-formulation promoter of this invention contains Quercetin 3-O-β-D-glucopyranoside as an active substance.

The human fibroblast-collagen grating-formulation promoter of this invention, according to the above features 13 to 18, allows cherry-derived extract, which is safe for food, to promote effectively human fibroblast collagen grating formulation, thus providing a material for foods, medicines, cosmetics and other products which are helpful in effectively preventing or inhibiting the skin from aging.

19. The AGE production inhibitor within the fibroblast of this invention contains cherry-tree extract and/or its processed substances as active substances.
20. The AGE production inhibitor within the fibroblast of this invention contains cherry-blossom extract and/or its processed substance as an active substance.
21. The AGE production inhibitor within the fibroblast of this invention contains cherry-leaf extract and/or its processed substance as an active substance.
22. The AGE production inhibitor within the fibroblast of this invention contains at least one active substance selected from among this group of compounds, i.e. 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside and Quercetin 3-O-(6"-malony)-β-D-glucopyranoside.

23. The AGE production inhibitor within the fibroblast of this invention contains 1-O-(E)-Caffeoyl-β-D-glucopyranoside as an active substance.

24. The AGE production inhibitor within the fibroblast of this invention contains Quercetin 3-O-β-D-glucopyranoside as an active substance.

The AGE production inhibitor within the fibroblast of this invention, according to the above features 19 to 24, allows cherry-derived extract, which is safe for food, to effectively inhibit AGE production within the fibroblast, thus providing a material for foods, medicines, cosmetics and other products which are helpful in effectively preventing or inhibiting the skin from aging.

25. The cherry-tree extract of this invention holds at least one active substance selected from among this group of compounds, i.e. 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-β-D-glucopyranoside, Kaempferol 3-O-(6"-malony)-β-D-glucopyranoside, and Quercetin 3-O-(6"-malony)-β-D-glucopyranoside.

26. The cherry-tree extract of this invention holds all of the substances of this group of compounds, i.e. 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and Quercetin 3-O-(6"-malony)-β-D-glucopyranoside.

27. The cherry-tree extract of this invention holds all compounds, 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, Quercetin 3-O-(6"-malony)-β-D-glucopyranoside and said cherry-tree extract is obtained by a manufacturing method having the following three steps:
(a) extracting one or both cherry blossom extract and the cherry leaf extract with 20 to 50 wt % hydrous ethanol,
(b) absorbing the extract obtained in step (a) by an absorbent comprising porous synthetic resin, elute the extract in water and remove the eluted extract, and
(c) after step (b) further eluting the eluted extract with a lower alcohol content (carbon numbers 1 to 5), and then concentrate the further eluted extract.

28. The AGE production inhibitor of this invention holds cherry-tree extract and/or its processed active substance according to the above feature 27.

29. The apoptosis inhibitor of this invention holds cherry-tree extract and its processed substance as an active substance, according to the above feature 27, and inhibits fibroblast apoptosis caused by the CML-collagen (i.e. Carboxymethyl lysine-collagen) which is an AGE.

30. The human fibroblast-collagen grating-formulation promoter of this invention holds cherry-tree extract and/or its processed substance as an active substance according to the above feature 27.

31. The AGE production inhibitor within the fibroblast of this invention holds cherry-tree extract and/or its processed substance as an active substance according to the above feature 27.

32. The agent, to prevent and cure the diabetic complications, of this invention holds cherry-tree extract and/or its processed substance as an active substance according to the above feature 27.

33. The agent, to prevent the skin from aging and to improve it, of this invention holds cherry-tree extract and/or its processed substance as an active substance according to the above feature 27.

The invention, according to the above features 25 to 33, allows the cherry-derived extract, which is safe for food, to inhibit AGE production effectively without side effects, thus providing a material for foods, medicines, cosmetics and other products which are helpful in effectively preventing or treating diabetic complications.

The invention, according to the above features 25 to 33, also effectively inhibits fibroblast apoptosis caused by CML-collagen (Carboxymethyl lysine-collagen), thus effectively promoting the human fibroblast-collagen grating-formulation, thus effectively inhibiting AGE production within the fibroblast, thus providing a material for foods, medicines, cosmetics and other products which are helpful in effectively preventing the aging of the skin and for improving it.

MODELS FOR CARRYING OUT THE INVENTION

Figure 1:
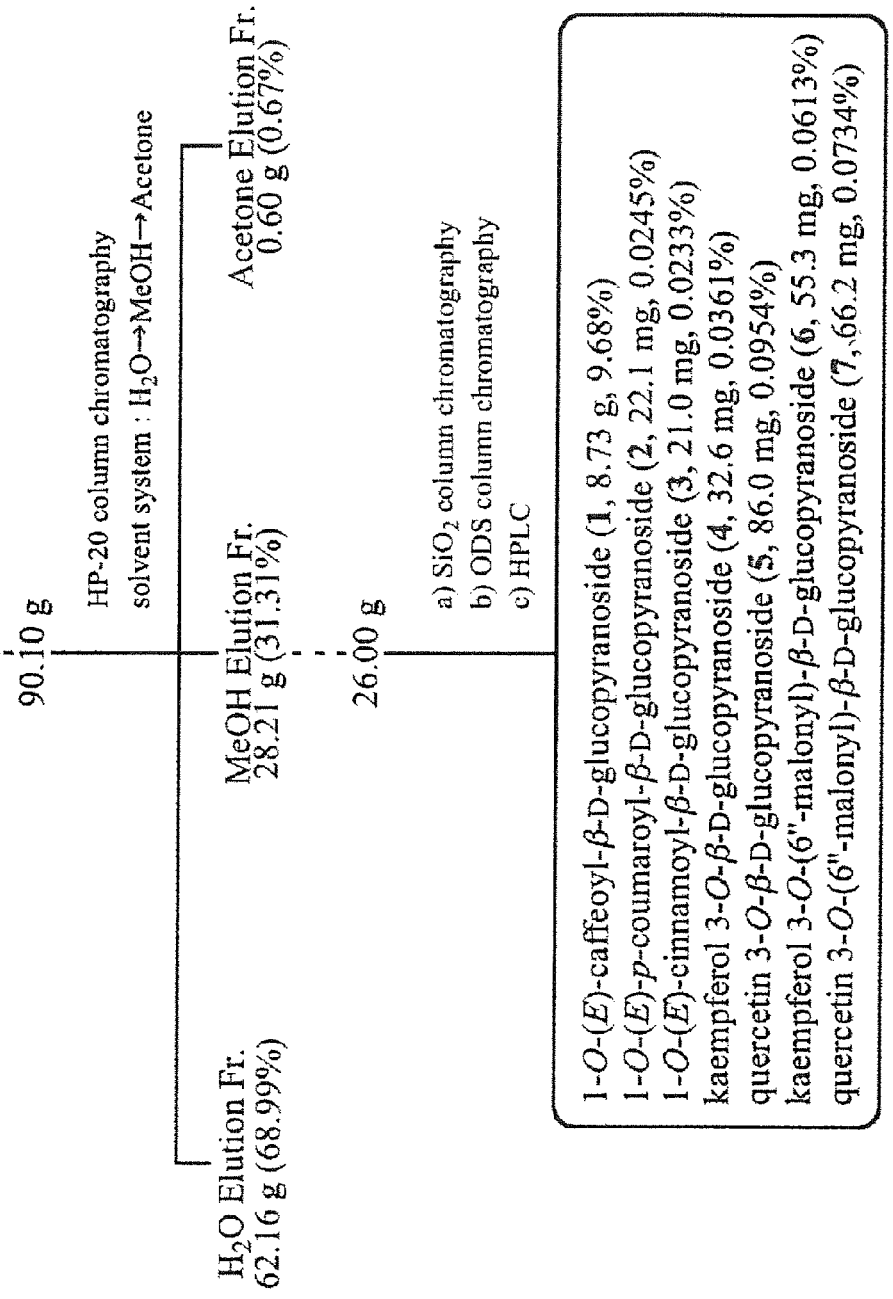
FIG. 1 is a chart explaining the search for the substances contained in the cherry-blossom extract.

Hereinafter, examples of this invention are described.
Of this invention, the AGE production inhibitor and fibroblast apoptosis inhibitor and human fibroblast-collagen grating-formulation promoter and AGE production inhibitor within the fibroblast and cherry extract (hereinafter collectively referred to as the AGE production inhibitor) contain, as a bioactive substance, at least one substance selected from among 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside and Quercetin 3-O-(6"-malony)-β-D-glucopyranoside.

1-O-(E)-Caffeoyl-β-D-glucopyranoside is a compound as described in Formula 1, below.

Formula 1

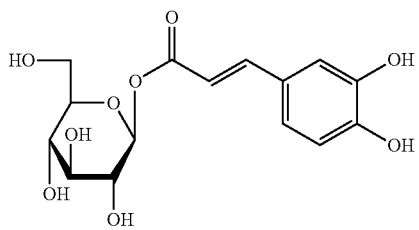

1-O-(E)-caffeoyl-β-D-glucopyranoside

1-O-(E)-Coumaroyl-β-D-glucopyranoside is a compound as described in Formula 2, below.

Formula 2

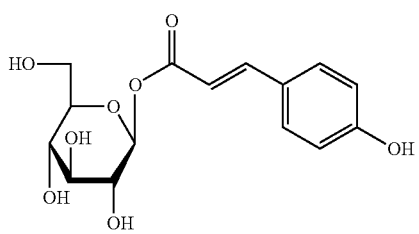

1-O-(E)-coumaroyl-β-D-glucopyranoside

1-O-(E)-Cinnamoyl-β-D-glucopyranoside is a compound as described in Formula 3, below.

Formula 3

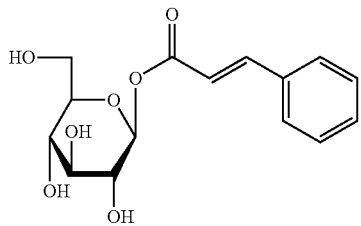

1-O-(E)-cinnamoyl-β-D-glucopyranoside

Kaempferol 3-O-β-D-glucopyranoside is a compound as described in Formula 4, below.

Formula 4

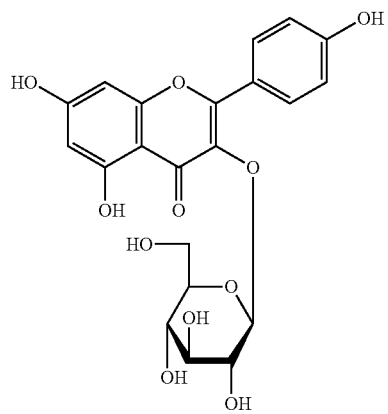

kaempferol 3-O-β-D-glucopyranoside

Quercetin 3-O-β-D-glucopyranoside is a compound as described in Formula 5, below.

Formula 5

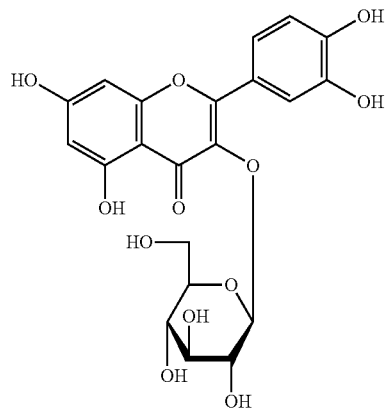

quercetin 3-O-β-D-glucopyranoside

Kaempferol 3-O-(6"-malony)-β-D-glucopyranoside is a compound as described in Formula 6, below.

Formula 6

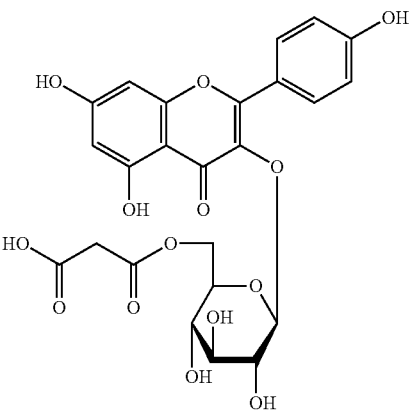

kaempferol 3-O-(6"-malonyl)-β-D-glucopyranoside

Quercetin 3-O-(6"-malony)-β-D-glucopyranoside is a compound as described in Formula 7, below.

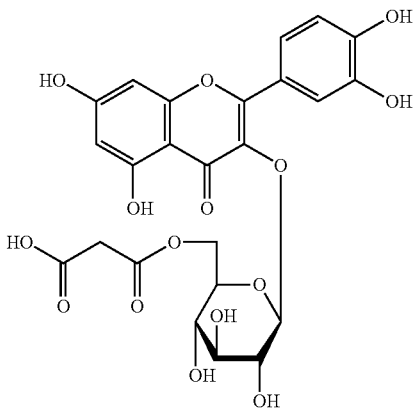

quercetin 3-O-(6"-malonyl)-β-D-glucopyranoside

It is preferable that AGE production inhibitor of this invention contain at least the compound 1-O-(E)-Caffeoyl-β-D-glucopyranoside (Formula 1) or Quercetin 3-O-β-D-glucopyranoside (Formula 5), which are selected from among the compounds, as described in Formulae 1 to 7, or especially the compound, 1-O-(E)-Caffeoyl-β-D-glucopyranoside (Formula 1).

Any method used in obtaining the compound as described in Formulae 1 to 7, above, is not specifically limited. Such a compound is, however, preferably to be extracted from plants, which makes it simple to obtain. Also, when extracting the compound from plants, it is preferable to extract it from the cherry tree.

Cherry blossom (refered to as Sakura in Japanese) is the generic name of the Genus *Cerasus* of Rosaceae, excluding apricots and peaches, and refers to plants belonging to Subgenus *Cerasus*.

The types of cherry blossoms (Sakura) used of this invention are not specifically limited. Cherry blossoms of this invention include, for example, *prunus yamazakukra* (*Cerasus jamasakura*), *edohigan* (*Cerasus spachiana* Lavalee ex H.Otto var. *spachiana* forma *ascendens* (Makino) H.Ohba), *mamezakura* (*Prunus incisa* Thunb. ex Murray) *choujizakura* (*Prunus apetara* Fr.et Sav.), *miyamazakura* (*Prunus maximowiczii* Rupr.), *shinamizakura* (*Prunus pseudo-cerasus* Lindl.) and others, but not limited to these.

The part of the cherry, which is used for the material of this invention, is not specifically limited but includes its leaf, stem, trunk, blossom, fruit and other parts. However, it is preferable to use the cherry leaf or blossom.

If extraction is done by using a polar solvent, the type of such a polar solvent is not limited but includes water, methanol, ethanol, isopropanol, acetone, 1,3-butylene glycol, ethylene glycol, propylene glycol, glycerin, acetic acid, ethyl acetate, ether, hexane and others. Of these, water, methanol, and ethanol are especially preferable, which efficiently extracts the active substance. Also, only one or more solvents from among the polar solvents, above, can be used.

When using water as an extracting solvent, the extraction temperature is to be set between 20 and 100 degrees centigrade, preferably between 40 and 70 degrees centigrade. If the temperature is too low, the active substance will not efficiently be extracted. On the other hand, if the temperature is too high, cyanogen compounds contained in the cherry-tree (sakura) will be eluted and remain in the water, and the active substance will be degraded in such a high temperature, which is not preferable, either. The types of water used for the extraction are not specifically limited but include tap water, distilled water, mineral water, ionized alkaline water and others.

When using aqueous alcohol as an extracting solvent, the concentration of alcohol is preferably to be set at 25 to 50 wt % (percent by weight), preferably at 25 to 30 wt %. If the level of alcohol concentration is below 20 wt %, it will be hard to get a high level of active substance. Contrarily, if the concentration of alcohol is over 50 wt %, the yield will be low, due to impurities or the like.

Also, in case where the concentration of alcohol is 30 wt % or more, the extraction temperature is preferably to be set at 0 to 95 degrees centigrade, more preferably at 0 to 60 degrees centigrade. As for the extraction of aqueous ethanol, it is preferable to repeat the extractions in various concentrations so as to improve the content rate of the active substance.

Also, when conducting an extraction with a polar solvent, the method of extraction is not specifically limited. The method of the extraction, for instance, includes a continuous extraction, a soaking extraction, a countercurrent extraction or any other extraction which can be used with any optional equipment at room temperature or by heating under reflux. Also, any one, or any combination of the above methods can be used for the extraction. Furthermore, the extraction can be conducted once or more than once.

As for the specific extraction method, put the extraction ingredient into the processing vessel filled with extracting solvent, and stir it so that the active substance seeps into the solvent.

For instance, when using hydrous ethanol as the extracting solvent, the extraction is conducted with the extracting solvent approximately 3 to 100 times as much weight as the extraction ingredient, from one to 150 minutes. After the active substance seeps into the solvent, filter it and remove the residue to obtain the extracted liquid. After that, according to the ordinary method, apply the dilution, concentration, drying, refining method or the like to the extracted liquid, so as to obtain the extract containing polyphenol, as described in the above Formulae 1 to 7 or the like.

Also, the refining method includes, for example, an activated carbon treatment, a resin absorption treatment, a silica gel treatment as well as another method using ion-exchange resin, and liquid-liquid countercurrent distribution, and membrane separation, or the like.

In addition, when the extraction is done by supercritical extraction, the supercritical fluid is not specifically limited but includes, for instance, carbon dioxide, nitrogen or the like, of which one or more fluids can be used at the same time. However, carbon dioxide is preferable, since it can easily elute the active substance. Also, the known conventional method of extraction can also be used. After the extraction, according to the ordinary method, apply the dilution, concentration, drying, refining method or the like to the extracted liquid, so as to obtain the extract containing polyphenol, as described in the above Formulae 1 to 7, or the like.

To obtain the polyphenol, as described in the above Formulae 1 to 7, it is preferable to use the following processes:
(a) extract the cherry blossom extract and/or the cherry leaf extract with 20 to 50 wt % hydrous ethanol,
(b) absorb the extract obtained in Process (a) by absorbent, elute the extract in water and remove the eluted extract, and
(c) elute the extract with an aqueous solvent, and then concentrate the eluted extract.

Using the above processes efficiently obtains the extract containing a high level of polyphenol, as described in the above Formulae 1 to 7.

As for the absorbent used in the above referenced process (b), one or more absorbents can be selected and used from among the known conventional absorbent such as an ion-exchange resin, a synthetic absorbent resin, an activated carbon, a chelating resin, silica gel, an alumina gel series absorbent, a porous glass or the like. It is preferable to use a column chromatography with porous synthetic absorbent resin such as DIAION®HP-20 (Mitsubishi Chemical Corporation), SEPABEADS®SP-207 (Mitsubishi Chemical Corporation) or the like.

As for the aqueous solvent used in the above referenced process (c), a lower alcohol content (carbon numbers 1 to 5) can be used. Methanol and/or ethanol is especially preferable.

The AGE production inhibitor or the like of this invention effectively inhibits AGE production and prevents diabetic complications such as nephropathy, retinopathy or the like. Also, it especially inhibits AGE production within the fibroblast to improve the crosslink of the collagen part of the skin, thus preventing the skin from hardening. Moreover, it inhibits fibroblast apoptosis occurring after the production of AGE, thus retaining the elasticity of the skin, thus preventing flecks and dullness of the skin. Furthermore, it improves collagen cross-linking after AGE production, thus preventing the skin from hardening.

The AGE production inhibitor or the like of this invention can be used as an ingredient for any food and drink such as, edible oils (salad oils), confectionary (chewing gums, candies, caramels, chocolates, cookies, jellies, gummies, tablet shaped sweets or the like), noodles (Japanese buckwheat noodles called Soba, Japanese wheat noodles called Udon, Chinese noodles called Ramen or the like), dairy food (milk, ice cream, yogurt, or the like), seasoning (fermented bean paste called Miso, Soy sauce called Shoyu, or the like), soups, drinks (juice, coffee, black tea, green tea, carbonated drink, sports supplement drinks or the like) including general foods and healthy food (tablet type, capsule type or the like), nutritional supplements (nutritious supplement drink or the like). The AGE production inhibitor or the like of this invention can be used for the above foods and drinks.

According to the type of the above foods and drinks, the following ingredients can be added: Glucose, fructose, sucrose, maltose, sorbitol, stevioside, corn syrup, lactose, citric acid, tartaric acid, malic acid, succinic acid, lactic acid, L-ascorbic acid, dl-α-tocopherol, sodium erythorbate, glycerin, propylene glycol, glycerin fatty acid ester, polyglycerol fatty acid ester, sucrose fatty acid ester, sorbitan fatty acid ester, propylene glycol fatty acid ester, Arabian gum, carrageenan, casein, gelatin, pectine, agar-agar (gelatin made from seaweed), vitamin B family, nicotinic-acid amide, pantothenate acid calcium, amino acids, calcium salts, pigment, aroma chemicals, preservatives, or the like.

Also, other antioxidants or compounding ingredients of healthy food include the antioxidant "reduced ascorbic acid" or vitamin C and also the antioxidants, vitamin E, reduced glutacin, tocotrienol, vitamin A derivative, lycopene, rutin, β-cryptoxanthin, astaxanthin, zeaxanthin, fucoxanthin, uric acid, ubiquinone, coenzyme Q-10, folic acid, garlic extract, allicin, sesamin, lignans, catechin, isoflavones chalcone, tannins, flavonoids, coumarin, isocoumarines, blueberry extract, ingredients for healthy food (V. (vitamin) A, V.B1, V.B2, V.B6, V.B12, V.C, V.D, V.E, V.P, choline, niacin, pantothenic acid, calcium folic acid, EPA, oligosaccharide, dietary fiber, squalene, soybean lecithin, taurine, dunalliela, protein, octacosanol, DHA, egg-yolk lecithin, linoleic acid, lactoferrin, magnesium, zinc, chrome, selenium, kalium, hem iron, oyster extract, chitosan, chitin oligosaccharides, collagen, chondroitin, elastin, turmeric, sweetroot, extract of Chinese wolfberry fruit called kukoshi, cinnamon, may, ginger, bracket fungus, shijimi clam (corbicula japonica) extract, snapping turtle, sweetroot, lycii fructus, cinnamomi cortex, hawthorn, plantain, chamomilla, chamomile, dandelion, hibiscus, honey, pollen, royal jelly, lime, lavender, rose hip, rosemary, sage, bifidobacteria, streptococcus faecalis, lactobacillus, wheat germ oil, sesame oil, perilla oil, soybean oil, medium chain fatty acid, agaricus, ginko biloba extract, chondroitin, brown rice germ oil, leechee, onion, DHA, EPA, DPA, rubus suavissimus s.lee, plant worm (cordyceps sineusis saccardo), garlic, larvae of a bee, papaya, pu-erh-tea, propolis, Acer nikoense, hericium erinaceum, royal jelly, saw palmetto, hyaluronic acid, gaba, harp seal oil, shark cartilage, lecithin, phosphatydyl serine, panax notoginseng, mulberry leaf, soybean extract, echinacea purpurea, acanthopanax senticosus, barley extract, olive leaf, olive, gymnema, banaba, salacia reticulata, garcinia, chitosan, saint john's wort, jujube, carrot, passion flower, broccoli, placenta, coix lacryma-bobi, grape seed, peanut skin, bilberry, black cohosh, milk thistle, laurel, sage, rosemary, apocynum venetum, black vinegar, bitter gourd, maca, carthamus tinctorius, linseed, oolong tea, flower aculeus, caffeine, capsaicin, xylo-oligosaccharide, glucosamine, buckwheat, citrus, dietary fiber, protein, prune, spirulina, young green barley leaf, nucleic acid, natural yeast, shiitake mushroom (lentinus edodes), Japanese plum, amino acid, extract of deep sea shark, morinda citrifolia, oyster, snapping turtle, championion, common plantain, acerola, pineapple, banana, peach, apricot, melon, strawberry, raspberry, orange, fucoidan, acer nikoense, cranberry, zinc, iron, ceramide, silk peptide, glycine, niacin, chaste tree, ceramide, L-cysteine, red grape juice, millet, horsetail, bition, centrlla asiatica, lonicera caerulea, pycnogenol, petasites japonicus, rhubarb, clove, pu-erh, citric acid, beer yeast, mellilot, black zinger, ginger, curcuma zedoaria, nattokinase, ang-khak (Chinese red rice), tocotrienol, lactoferrin, tartary buckwheat, cocoa, houttuynia cordata, kiwi fruit, piper longum, lotus leaf, pfaffia and star fruit.

A more specific use of the extracting method is herein described. Firstly, spray-dry or freeze-dry the cherry-tree extract with powdered cellulose, then make it a powder, a granule, a tablet, or liquid to easily use with different kinds of food and drinks (ready-to eat meals or the like). Also, it is possible to dissolve the cherry-tree extract, for instance, oil and fat, ethanol, glycerin, or a mixture of these substances, and to use such a liquid for dry food or drinks. Also it is possible to make it into a powder or granule by mixing it with a binder such as Arabian gum, dextrin, or the like to add to dry food or drinks.

The total amount of the active substance of the AGE production inhibitor or the like of this invention, which is added to the food and drinks, is preferably 1 to 20 wt % or less, since the major objective of this invention is health maintenance.

The AGE production inhibitor or the like of this invention can be used as the raw material of medicines (including drugs and quasi-drugs). The AGE production inhibitor or the like of this invention can be appropriately mixed with raw materials for drug formulations, for instance, vehicles (glucose, sucrose, white soft sugar, sodium chloride, starch, calcium carbonate, kaolin, crystalline cellulose, cacao oil, hydrogenated vegetable oil, talc, or the like), binders (distilled water, normal saline solution, ethanol in water, ethanolic solution, simple syrup, dextrose in water, starch solution, gelatin solution, carboxymethyl cellulose, potassium phosphate, polyvinyl pyrrolidone, or the like), disintegrating agents (alginate sodium, agar-agar, sodium hydrogen carbonate, sodium lauryl sulphate, stearic acid monoglyceride, starch, lactose, powdered aracia, gelatin, ethanol, or the like), suppressive agents for disintegration (white soft sugar, stearin, cacao oil, hydrogenated oil, or the like), absorption promoters (quaternary ammonium base, sodium lauryl sulphate, or the like), adsorbents (glycerin, starch, lactose, kaolin, bentonite, silic acid, or the like), lubricant agents (purified talc, stearate, polyethyleneglycol, or the like)

The AGE production inhibitor or the like of this invention can be orally administered in the form of tablets, pills, soft or hard capsules, subtle granules, powders, granules, liquids, or the like. However, it can also be parenterally administered in the different forms of solution or together with a dispersant, a suspending agent, a stabilizer, or the like such as a medical skin patch, a lotion, an ointment, a cream or the like.

The applied dose can be adjusted according to the method of administration, the condition of the disease, the age of the patient, or the like. However, adults can normally take approx. 1 to 1,000 mg of an active substance per day, while children can take 0.5 to 500 mg per day. The compounding ratio of the AGE production inhibitor or the like of this invention can be adjusted according to the mode of administration. When the dietetic composition is orally administered or mucosally administered, the applied dose is preferably 0.3 to 15.0 wt %. When the dietetic composition is parenterally administered, the dose is preferably 0.01 to 10 wt %. The dose varies depending on the conditions. Therefore, a dose which is less than the above-stated amount may be sufficient, or a greater amount may sometimes be needed.

The AGE production inhibitor or the like of this invention can be mixed with cosmetics such as emulsions, soaps, facial cleansers, bath agents, creams, skin lotions, colognes, shaving creams, shaving lotion, beauty oils, tanning lotions, sunscreen lotions, face powders, foundations, perfumes, facial masks, nail creams, nail enamels, nail-polish removers, eyebrow pencils, blushers, eye creams, eye shadows, mascaras, eye liners, sticks, lip creams, shampoos, hair conditioners, hairdyes, dispersion liquids, cleansing preparations, or the like. Also, the AGE production inhibitor or the like of this invention can be mixed with drugs and quasi-drugs such as ointments, cream pharmaceuticals, liquids for external use or the like.

Within the functional range of the AGE production inhibitor or the like of this invention, the above items for external skin use can be also mixed with the ingredients of cosmetics, quasi-drugs, or the like. Those ingredients include, for example, oil, higher alcohol, fatty acids, ultraviolet absorbers, powders, pigments, surface active agents, polyhydric alcohol and sugar, polymers, biologically active ingredients, solvents, antioxidants, aroma chemicals (perfume material), antiseptics. However, those ingredients usable in the present invention are not limited to these examples.

(1) Specific Examples of Oil

Ester-Type Oil Phase Ingredient:

Triglyceryl 2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoarachyl neopentanoate, caprylic-capric acid triglyceride, trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di(caprylate/caprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin oleate, polyglycerin isostearate, dipropyl carbonate, dialkyl carbonate (C12-18), triisocetyl citrate, triisoarachyl citrate, triisooctyl citrate, lauryl lactate, myristyl lactate, cetyl lactate, octyldecyl lactate, triethyl citrate, acetyltriethyl citrate, acet-yltributyl citrate, trioctyl citrate, diisostearyl malate, 2-ethylhexyl hydroxystearate, 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate. From among the above ingredients, one only can be used, or two or more can be used together.

Hydrocarbon-Type Oil Phase Ingredient:

Squalane, liquid paraffin, α-olefin oligomer, isoparaffin, ceresin, paraffin, liquid isoparaffin, polybutene, microcrystalline wax, Vaseline or the like.

Animal and plant oil, hardened oil thereof, and wax of natural origin: Animal oils and hardened oils thereof, such as beef tallow, hardened beef tallow, lard, hardened lard, horse oil, hardened horse oil, mink oil, orange roughy oil, fish oil, hardened fish oil and egg yolk oil; plant oils and hardened oils thereof such as avocado oil, almond oil, olive oil, cacao oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, conoanut oil, hardened cocoanut oil; and waxes such as beeswax, high acid number beeswax, lanolin, reduced lanolin, hardened lanolin, liquid lanolin, carnauba wax and montan wax. From among the above ingredients, one only can be used, or two or more can be used together.

Silicone-type oil phase ingredient:

Dimethylpolysiloxane, methylphenylpolysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxanemethylcetyloxysiloxane copolymer, dimethylsiloxane-methylstearoxysiloxane copolymer, alkyl-modified organopolysiloxane, terminal-modified organopolysiloxane, amino-modified silicone oil, amino-modified organopolysiloxane, dimethiconol, silicone gel, acryl silicone, trimethylsiloxysilicic acid and silicone RTV rubber. From among the above ingredients, one only can be used, or two or more can be used together.

Fluorine-Type Oil Phase Ingredient:

Perfluoropolyether, fluorine-modified organopolysiloxane, fluorinated pitch, fluorocarbon, fluoroalcohol and fluoroalkyl-polyoxyalkylene-comodified organopolysiloxane. From among the above ingredients, one only can be used, or two or more can be used together.

(2) Specific Examples of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol. From among the above ingredients, one only can be used, or two or more can be used together.

(3) Specific Examples of Fatty Acid

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid and 2-ethylhexanoic acid. From among the above ingredients, one only can be used, or two or more can be used together.

(4) Specific examples of ultraviolet absorber

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomenthyl salicylate, benzyl cinnamate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenonedisulfonate, dihydroxybenzophenone, dihydroxydimethoxybenzophenone, hydroxyoctoxybenzophenone, tetrahydroxybenzophenone, butylmethoxydibenzoylmethane, 2,4,6-trianilino-p-(carbo-2-ethylhexyl-1-oxy)-1,3,5-triazine, 2-(2-hydroxy-5-methylphenyl)benzotriazole, methyl-0-aminobenzoate, 2-ethylhexyl-2-cyano-3,3-diphenylacrylate, phenylbenzimidazole sulfuric acid, 3-(4-methylbenzylidene) camphor, isopropyldibenzoylmethane, 4-(3,4-dimethoxyphenylmethylene)-2,5-doxy-1-imidazolidinepropionate, and polymer derivatives and silane derivatives thereof. From among the above ingredients, one only can be used, or two or more can be used together.

(5) Specific Examples of Powder and Pigment

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. From among the above ingredients, one only can be used, or two or more can be used together.

The shape (e.g., sphere, bar, needle, plate, amorphous, scale, spindle) and the particle size of these powders are not particularly limited. These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment. From among the above ingredients, one only can be used, or two or more can be used together.

(6) Specific Examples of Surfactant

Anionic Surfactant:

Fatty acid soap, a-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt and perfluoroalkylphosphoric acid ester. From among the above ingredients, one only can be used, or two or more can be used together.

Cationic Surfactant:

Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate and lanolin derivative quaternary ammonium salt. From among the above ingredients, one only can be used, or two or more can be used together.

Amphoteric Surfactant:

Carboxybetaine type, amidobetaine type, sulfobetaine type, hydroxysulfobetaine type, amidosulfobetaine type, phosphobetaine type, aminocarboxylate type, imidazoline derivative type and amidoamine type. From among the above ingredients, one only can be used, or two or more can be used together.

Nonionic Surfactant:

Propylene glycol fatty acid ester, glycerin fatty acid ester, polyglycerin fatty acid ester, sorbitan fatty acid ester, POE sorbitan fatty acid ester, POE sorbitol fatty acid ester, POE glycerin fatty acid ester, POE alkyl ether, POE fatty acid ester, POE hydrogenated castor oil, POE castor oil, POE-POP copolymer, POE-POP alkyl ether, polyether-modified silicone lauric acid alkanolamide, alkylamine oxide and hydrogenated soybean phospholipid. From among the above ingredients, one only can be used, or two or more can be used together.

Natural-Type Surfactant:

Lecithin, saponin and sugar-type surfactant. One ingredient only can be used, or two or more can be used together.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose and pullulan. Chemically modified products thereof can also be used. From among the above ingredients, one only can be used, or two or more can be used together.

(8) Specific Examples of Polymer Compound

Anionic polymer compounds such as acrylic acid ester/methacrylic acid ester copolymer (PLUS-SIZE, produced by Sogokagaku K. K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/ acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/ dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabi, crystal cellulose, arabino galactan, karaya gum, tragacanth gum, alginic acid, albumin, casein, cardrun, gellan gum and dextran, can also be suitably used. From among the above ingredients, one only can be used, or two or more can be used together.

(9) Specific Examples of Biologically Active Ingredient

The biologically active ingredient may include substances which are capable of imparting some biological activity to skin, when such a substance is applied to the skin. Specific examples thereof may include: whitening ingredient, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, sabdariffa extract, pyracantha fortuneana fruit extract, cinchona extract, cucumber extract, guanosine, gardenia extract, sasa albomarginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocos extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, coix seed extract, mugwort extract, lavender extract, apple extract, lettuce extract, lemon extract, Chinese milk vetch extract, rose extract, rosemary extract, Roman chamomile extract and royal jelly extract, strawberry extract, piper longum extract, lotus leaf extract, pfaffia extract, star fruit extract or the like.

Other examples may include biopolymers such as deoxyribonucleic acid, mucopolysaccharide, sodium hyaluronate, sodium, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as E-aminocaproic acid, glycyrrhizic acid, -glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SASANISHIKI extract. From among the above ingredients, one only can be used, or two or more can be used together.

(10) Specific Examples of Antioxidant

Sodium hydrogensulfite, sodium sulfite, erythorbic acid, sodium erythorbate, dilauryl thiodipropionate, tocopherol, tolylbiguanide, nordihydroguaiaretic acid, parahydroxy anisole, butylhydroxy anisole, dibutylhydroxy toluene, ascorbyl stearate, ascorbyl palmitate, octyl gallate, propyl gallate, carotenoid, flavonoid, tannin, lignin, saponin and plant extracts having antioxidant effect, such as apple extract and clove extract. From among the above ingredients, one only can be used, or two or more can be used together.

(11) Specific Examples of Solvent

Purified water, ethanol, lower alcohol, ethers, LPG, fluorocarbon, N-methylpyrrolidone, fluoroalcohol, volatile linear silicone and next generation freon (such as fluorocarbon, chlorofluorocarbon, CFC). From among the above ingredients, one only can be used, or two or more can be used together.

EXAMPLE

Examples of this invention are described here, which identify the AGE inhibitory activity, or the like, of the compound obtained by this invention and which show that the scope of this invention is not limited to its products and manufacturing methods.

(1) Method for Producing Extract of Cherry-Tree (Cherry Blossom, Cherry Leaf):

Using cherry blossoms (referred to as "yaezakura" in Japanese, *Prunus lannesiana* Wils. cv. Sekiyama), an extraction was done with 30%(w/w) hydrous ethanol at 60 degree centigrade for one hour. After that, filtering and concentrating were done to obtain the cherry-blossom extract of a yield of 5 wt %. In the same way, cherry-leaf extract was obtained of a yield of 4 wt %. Then, the cherry-blossom extract and cherry-leaf extract were applied, per Example 1 and Example 2, respectively.

(2) Method for Separating the Active Substance from Cherry-Blossom Extract:

The search for substances held in the cherry-blossom extract is shown in FIG. 1. In other words, Example 1, the cherry-blossom extract (90.10 grams) is suspended within the chromatography column (HP-20, Mitsubishi Chemical Corporation) to obtain eluted water ($H_2O$) [of] (62.16 g, 68.88%), eluted methanol (MeOH) [of] (28.21 g, 31.31%) and eluted acetone (Acetone) [of] (0.60 g, 0.67%).

Next, repeatedly separate and refine the eluted methanol (MeOH) of (26.00 g) within the normal-phased silica-gel chromatography column, within the reverse-phased ODS chromatography column and within the HPLC (high-performance liquid chromatography column) to isolate the known three-different phenylpropanoid glycosides: 1-O-(E)-Caffeoyl-β-D-glucopyranoside (8.73 g, 9.6%), 1-O-(E)-Coumaroyl-β-D-Glucopyranoside (22.1 mg, 0.0245%) and 1-O-(E)-Cinnamoyl-β-D-glucopyranoside (21.0 mg, 0.0233%), as well as the known four-different flavonoid glycosides: Kaempferol 3-O-β-D-glucopyranoside (32.6 mg, 0.0361%), Quercetin 3-O-β-D-glucopyranoside (86.0 mg, 0.0954%), Kaempferol 3-O-(6"-malony)-β-D-glucopyranoside (55.3 mg, 0.0613%) and Quercetin 3-O-(6"-malony)-β-D-glucopyranoside (66.2 mg, 0.0734%). (Examples 3 to 5 and 6 to 9).

The known compounds, above are identified by comparison of the literature values of 1H-NMR and 13C-NMR, Mass Spectral Database and optical rotation. Also, each yield (w/w) of the isolated substances, as shown in FIG. 1, means an isolated yield of the cherry-blossom extract, Example 1.

(3) Effect Confirmation Test (Test 1: Effect of AGE Production Inhibition)

To confirm the effect of the cherry-blossom extract and the cherry-leaf extract on the formation of AGE, the following tests were done.

Put the sample solution (100 mL) of the concentration of cherry-blossom extract (Example 1) and cherry-leaf extract (Example 2), as shown in the chart, below, into a phosphate buffer solution (pH: 7.4, 900 mL) containing D-glucose (10%) and into bovine serum albumin (fraction 5.1%) and leave it out at a temperature of 60 degrees centigrade for two days. Dilute the reaction solution with distilled water until the intensity of fluorescent light reaches about 500, thus determining its intensity (measurement wavelength: 370 nm, excitation wavelength: 440 nm). Also, the extract is to be diluted with distilled water, and the substance, after being dissolved in DMSO (dimethyl sulphoxide), is to be diluted with a phosphate buffer solution until DMSO concentration is of 1%. The result is shown in Chart 1, below. Each value in Chart 1 indicates an average value with standard error of the three examples. Asterisks (*, **) mean a significant difference (i.e. *: $p < 0.05$; **: $p < 0.01$) between the processed samples and the unprocessed samples as determined by Dunnett's Multiple Comparison Test.

CHART 1

AGE production inhibitory effect of cherry-blossom extract and its content substances

| | Inhibition Ratio (%) | | | | | | IC50 |
|---|---|---|---|---|---|---|---|
| | 1 (µg/mL) | 3 | 10 | 30 | 100 | 300 | (µg/mL) |
| Cherry-blossom extract | −8.6 ± 0.5 | −14.6 ± 0.7 | −10.8 ± 0.4 | −9.9 ± 0.6 | 15.1 ± 0.7** | 42.6 ± 3.2** | >300 |
| Cherry-leaf extract | −1.4 ± 0.1 | 2.8 ± 0.1 | 7.0 ± 0.1 | 21.6 ± 0.4** | 37.3 ± 1.4** | 49.8 ± 0.4** | >300 |
| 1-O-(E)-Caffeoyl-β-D-glucopyranoside | −3.3 ± 0.1 | 0.9 ± 0.1 | 10.7 ± 0.1** | 19.5 ± 0.3** | 25.0 ± 0.3** | 30.0 ± 0.4** | >300 |
| 1-O-(E)-Coumaroyl-β-D-glucopyranoside | −3.2 ± 0.1 | −8.2 ± 0.1** | −8.6 ± 0.1** | −8.9 ± 0.1** | −3.7 ± 0.1** | 11.6 ± 0.1** | >300 |
| 1-O-(E)-Cinnamoyl-β-D-glucopyranoside | −8.4 ± 0.1 | −10.4 ± 0.1 | −10.9 ± 0.4* | −7.8 ± 0.1 | 5.7 ± 0.1 | 23.3 ± 0.4** | >300 |
| Kaempferol 3-O-β-D-glucopyranoside | −8.4 ± 0.1** | −9.1 ± 0.2** | −2.0 ± 0.1 | 19.4 ± 0.1** | 45.0 ± 0.5** | 80.3 ± 0.7** | 102 |
| Quercetin 3-O-β-D-glucopyranoside | 8.5 ± 0.1** | 6.5 ± 0.1* | 27.6 ± 0.5** | 49.8 ± 0.7** | 74.2 ± 1.1** | 100.8 ± 0.6** | 30 |
| Kaempferol 3-O-(6"-malony)-β-D-glucopyranoside | −5.0 ± 0.1 | −8.5 ± 0.1 | 0.2 ± 0.1 | 20.5 ± 0.3** | 50.8 ± 0.4** | 91.7 ± 1.7** | 78 |
| Quercetin 3-O-(6"-malony)-β-D-glucopyranoside | −10.4 ± 0.9 | 1.9 ± 0.1 | 20.4 ± 0.3** | 43.7 ± 0.7** | 74.6 ± 0.7** | 103.9 ± 3.6** | 36 |
| Aminiguanidine hydrochloride | — | — | 1.4 ± 0.1 | 18.1 ± 1.1 | 42.6 ± 1.7** | 67.7 ± 1.6** | 138 |

Significant difference
*p < 0.05,
**p < 0.01

[Test 1: Result and Effect of Examples]

It is identified in Chart 1 that the cherry-blossom extract (Example 1) and cherry-leaf extract (Example 2), both in concentration of 100 to 300 μg/mL, inhibit the production of AGE.

Also, as shown in Chart 1, the main polyphenol of cherry blossom, i.e. 1-O-(E)-Caffeoyl-β-D-glucopyranoside (Example 3), in high concentration of 300 μg/mL, shows a 30% inhibitory activity. The inhibitory activity of a related compound with less hydroxyl, i.e. 1-O-(E)-Coumaroyl-β-D-Glucopyranoside (Example 4), and 1-O-(E)-Cinnamoyl-β-D-glucopyranoside (Example 5) is reduced. Contrarily, the inhibitory activity of flavonoid glycoside is generally much, and the inhibitory activity of Quercetin 3-O-β-D-glucopyranoside (Example 7) and Quercetin 3-O-(6"-malony)-β-D-glucopyranoside (Example 9) is much (1050), more than twice as much as the inhibitory activity of other compounds with Kaempferol as an aglycon. (1050: half-maximal (50%) inhibitory concentration)

[Test 2-1: Inhibitory Activity Against Fibroblast Apoptosis Caused by CML-Collagen]

It is known that the main AGE factor, CML-collagen (Carboxymethyl lysine-collagen), found in the skin, damages skin cells. Here, Test 2-1 verifies the beneficial activity of cherry-blossom extract (Example 1) upon human fibroblast apoptosis caused by CML-collagen.

(1) Method of Preparing CML-Collagen 50 mg of 1 mM HCL was added to 25 mL of bovine skin-derived collagen and dissolved for two hours incubation at the temperature of 37 degrees centigrade, and was shaken as needed. Then, PBS (pH7.4 25 mL) was added to sodium cyanoborohydride (1.42 g) and to glyoxylic acid (0.9 g) and mixed so as to react at the temperature of 37 degrees centigrade for 24 hours. The reaction solution was then put into a dialysis cell of 10,000 molecular mass for a dialysis-with-water test to be conducted for one day and for a dialysis-with-PBS to be conducted for six days. CML-collagen (21 mg) was obtained by freeze-drying the dialysate.

(2) Fibroblast Culture

Prior to the test below, a human diploid fibroblast (female/age 40/normal skin-derived/PDL20) was cultured in the medium of fetal calf serum (FCS) with penicillin (100 units/mL) and streptomycin (100 mg/mL).

The fibroblast (7×104 cells) was suspended in the D-MEM medium containing FCS (0.5%), penicillin (100 units/mL) and streptomycin (100 mg/mL) to be seeded within 96-well plates (100 mL/well). After 24 hours of culture, the dissolved CML-collagen solution (2 mg·mL) and the sample solution (13 mL) were added to the medium and cultured for 24 hours. Collagen, instead of CML-collagen, was added to Normal group.

(4) Cell Survival Rate and Apoptosis Measurement

Figure 2:
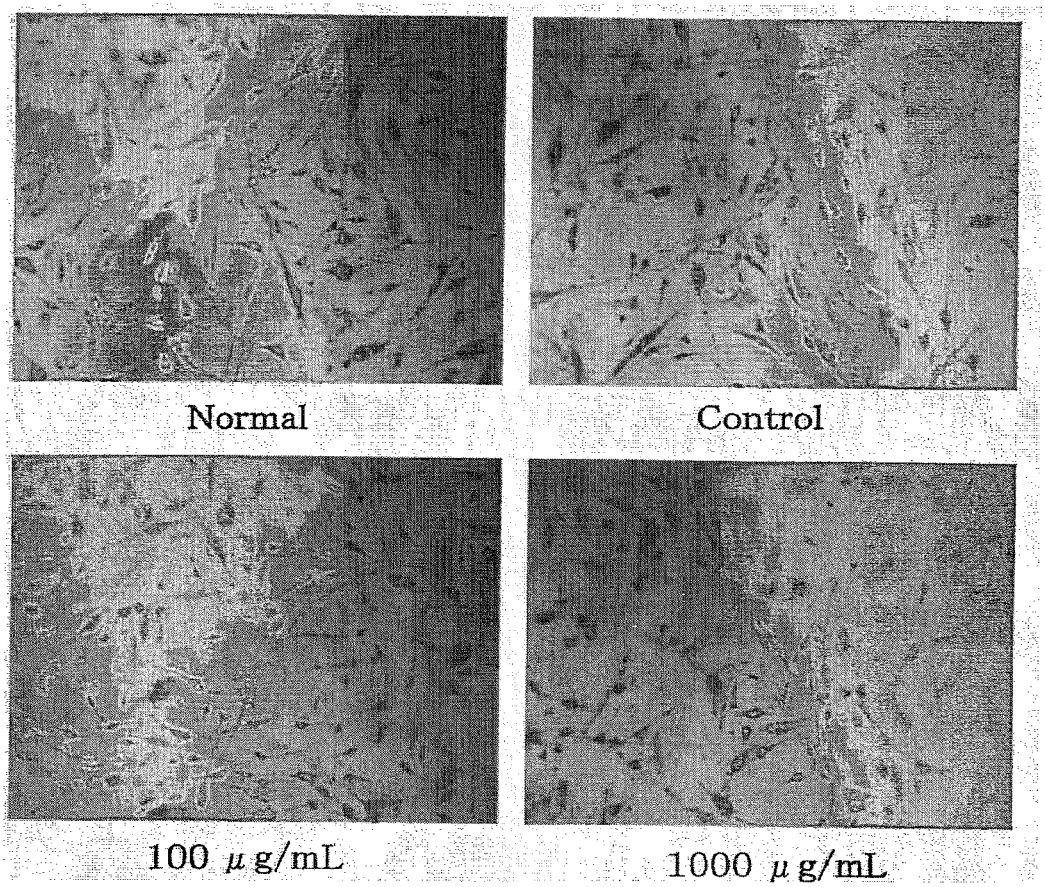
FIG. 2 is a microscopic image of fibroblast caused by CML-collagen (Carboxymethyl lysine-collagen) regarding the cherry blossom extract of the example of this invention.

The rate of cell survival was measured by MIT Assay. The result is shown in Chart 2. At the same time, a microscopic test was done, of which the result of formazan formation of fibroblast (×100) is shown in FIG. 2. Apoptosis was identified by measuring active caspase-3/7 by the fluorescence method, of which the result is shown in Chart 3, below. Each value of Charts 2 and 3 is indicated by the average value with standard error of the six examples. Asterisks (*, **) mean a significant difference (i.e. *: p<0.05; **: p<0.01) between the unprocessed samples and Dunnett's multiple comparison test, and f represents p<0.05 by Fisher's PLSD Test.

CHART 2

Effect of cherry-blossom extract against fibroblast cell survival rate (MTT Assay)

| | Concentration (μg/mL) | Absorbance of formazan formation (570 nm) |
|---|---|---|
| Normal | — | 0. 192 ± 0.007* |
| Control | — | 0. 172 ± 0.007 |
| Cherry-blossom extract | 10 | 0. 166 ± 0.002 |
| | 30 | 0. 169 ± 0.002 |
| | 100 | 0. 175 ± 0.002 |
| | 300 | 0. 174 ± 0.002 |
| | 1000 | 0. 185 ± 0.004 f |

N = 6, Average value ± standard error
*p < 0.05 (Dunnett's Test)
f: p < 0.05 (Fisger's PLSD Test)

CHART 3

Effect of cherry-blossom against fibroblast apoptosis (caspase-3/7 Assay)

| | Concentration (μg/mL) | Intensity of fluorescent light (Excitation 480 nm/Detection 530 nm) |
|---|---|---|
| Normal | — | 282 ± 9* |
| Control | — | 331 ± 12 |
| Cherry-blossom extract | 10 | 301 ± 13 |
| | 30 | 348 ± 11 |
| | 100 | 293 ± 16 f |
| | 300 | 245 ± 12* |
| | 1000 | 139 ± 5** |

N = 6, Average value ± standard error,
*p < 0.05,
**p < 0.01 (Dunnett's Test),
f: p < 0. 05 (Fisher's PLSD Test)

[Test 2-1: Result and Effect of Examples]

(1) Cell Survival Rate

According to Chart 2, above, the absorbent rate of the Control group is higher than that of the Normal group, and the cell survival rate was lowered due to CML-collagen. As shown in FIG. 2, the microscopic images identify the inhibition of formazan accumulation within the cell. By this situation, it is anticipated that fibroblast apoptosis is induced by CML-collagen. Contrarily, in the group of which 1000 mg/mL of the cherry-blossom extract (Example 1) is added, the formazan formation significantly increased.

(2) Apoptosis Inhibition

As shown in Chart 3, above, caspase-3/7 activity of the Control group increases compared to that of the Normal group, and it is identified that apoptosis is induced by the CML-collagen. Contrarily, in the Normal group of which the cherry-blossom extract (more than 100 mL) was added, caspase-3/7 activity decreased. When the volume of cherry-blossom extract was more than 300 mg/mL, caspase-3/7 activity was lower in the Control group than that in the Normal group, which suggests that the cherry-blossom extract possibly inhibits enzyme activity and enzyme expression of caspase-3/7.

[Test 2-2: Inhibitory Activity of Cherry-Blossom Extract, and Cherry-Leaf Extract and their Substances Against Fibroblast Apoptosis Caused by CML-Collagen]

Here, in Test 2-2, respecting the cherry-blossom extract (Example 1), and the cherry-leaf extract (Example 2) and the seven substances contained in the cherry-blossom extract (Example 1): 1-O-(E)-Caffeoyl-β-D-glucopyranoside, 1-O-(E)-Coumaroyl-β-D-Glucopyranosideand, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside and Quercetin 3-O-(6"-malony)-β-D-glucopyranoside (Examples 3 to 9), the activity against fibroblast apoptosis, caused by CML-collagen, was identified in the same way as in Test 2-1.

Also, in Test 2-2, PDL22-32 cells were used as the normal diploid fibroblast. As a target for comparison, aminoguanidine hydrochloride which is a medicine for the glycation inhibitor was examined in the same way. The result is indicated in Chart 4, below. Each value of Chart 4 indicates an average value with standard error of the five examples. Asterisks (*, **) mean a significant difference (i.e. *: p≤0.05, **: p<0.01) between processed samples and unprocessed samples with CML-collagen, determined by Dunnett's Multiple Comparison Test.

CHART 4

Effect of Cherry-blossom/Cherry-leaf extract against fibroblast apoptosis
(Caspase Assay)

| | Inhibition Ratio (%) | | | | |
|---|---|---|---|---|---|
| | 1 (μg/mL) | 3 | 10 | 30 | 100 |
| Cherry-blossom extract | — | | 61.8 ± 2.6 | | 77.1 ± 4.2* |
| Cherry-blossom leaf extract | (−13.2 ± 0.7) | | 62.7 ± 3.7 | 85.1 ± 3.1 | (176.7 ± 13.7)** |
| | (−24.5 ± 0.7) | | 46.9 ± 1.4 | 58.4 ± 1.9* | (135.2 ± 3.1)** |
| 1-O-(E)-Caffeoyl-β-D-glucopyranoside | 26.2 ± 0.5* | 37.6 ± 1.2 | 72.2 ± 2.7* | | |
| 1-O-(E)-Coumaroyl-β-D-glucopyranoside | 17.2 ± 0.5 | 7.1 ± 0.2 | 51.1 ± 1.9 | | |
| 1-O-(E)-Cinnamoyl-β-D-glucopyranoside | −11.8 ± 03 | 19.7 ± 0.9 | 48.6 ± 2.9 | | |
| Kaempferol 3-O-β-D-glucopyranoside | −0.7 ± 0.1 | 27.9 ± 1.1 | 100.7 ± 4.2 | | |
| Quercetin 3-O-β-D-glucopyranoside | 44.2 ± 1.5* | 39.0 ± 1.1* | 121.5 ± 5.4** | | |
| Kaempferol 3-O-(6"-malony)-β-D-glucopyranoside | −18.9 ± 0.6 | −17.3 ± 0.6 | 10.5 ± 0.5 | | |
| Quercetin 3-O-(6"-malony)-β-D-glucopyranoside | 21.8 ± 0.7 | 36.6 ± 1.4 | 98.4 ± 4.4* | | |
| Aminoguanidine Hydrochloride | | | | | 104.8 ± 34* |

Significant difference
*p < 0.05,
**p < 0.01

[Test 2-2: Result and Effects of Examples]

As shown in Chart 4, the cherry-blossom extract (Example 1, 10 to 100 mg/mL) lowered caspase-3/7 activity. From this result, it is suggested that the cherry-blossom extract (Example 1) inhibits apoptosis caused by CML-collagen. Among the contents, Quercetin 3-O-β-D-glucopyranoside (Example 7), shown to be the strongest substance in the AGE production inhibitory Test 1, had the strongest inhibitory activity. Similar compounds like Kaempferol 3-O-β-D-glucopyranoside (Example 6) and Quercetin 3-O-(6"-malony)-β-D-Glucopyranoside (Example 9) showed strong inhibitory activity. However, Kaempferol 3-O-(6"-malony)-β-D-glucopyranoside (Example 8) showed relatively weak activity. As for cinnamic acids, Kaempferol 3-O-β-D-glucopyranoside, which contains the highest level of cinnamic acid, showed especially strong inhibitory activity.

As such, it is thought that the cherry blossom extract (Example 1), and the cherry leaf extract (Example 2) and their active substances have AGE production inhibitory activity which inhibits fibroblast apoptosis caused by CML-collagen. In light of the above results, it is seen that these active substances function as a breaker that degrades CML-collagen, which is an AGE. Thus, the AGE production inhibitor of this invention can be used to as an AGE decomposition agent or as an AGE remover.

[Test 3: Promoting Activity of Fibroblast Collagen Grating Formation]

When fibroblast is cultured in the presence of collagen solution, collagen grating formation can be identified. In a similar test, when adding fibroblast that has been glycosylated by the intermediate product of glycation (glyoxal), it is known that the collagen grating formation is inhibited. Here, Test 3 showed the cherry-blossom extract inhibits formation of the collagen grating of glycated human fibroblast.

(1) Glycation of Fibroblast

The infant-derived NB1RGB (passage number 22) was suspended in the D-MEM complete media ($1.86 \times 10^4$ cells/mL). 15 mL each of it was seeded within each cell-culture dish of 14 cm in diameter. After 24 hours, each sample and glyoxal were added until the molecular mass of each dish became 200 mM and incubate the dishes for five days.

(2) Collagen Grating Formation

Bovine skin-derived collagen (25 mg) was dissolved in 0.1% acetic acid (8.3 mL). Then, a 10-times concentration of Hanks solution (1.66 L) was added. Then, 0.1% acetic acid (3.5 mL) was added. 1M NaOH was added to neutralize the solution, which was sterilized by filteration to obtain the collagen solution.

Figure 3:
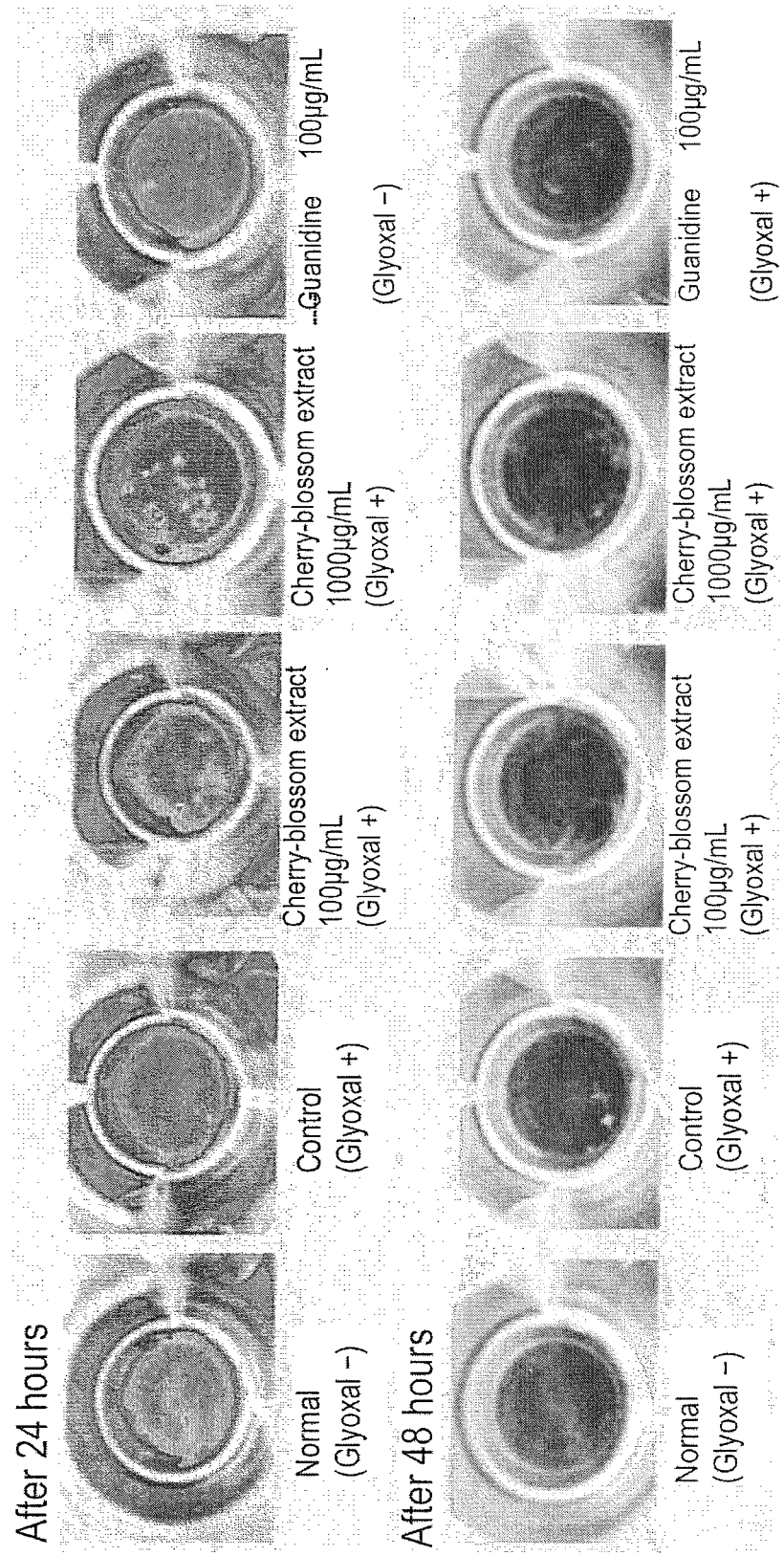
FIG. 3 is a megascopic image of 24 and 48 hours of a culture of collagen-grating formulations of fibroblasts glycosylated by glyoxal.
Figure 4:
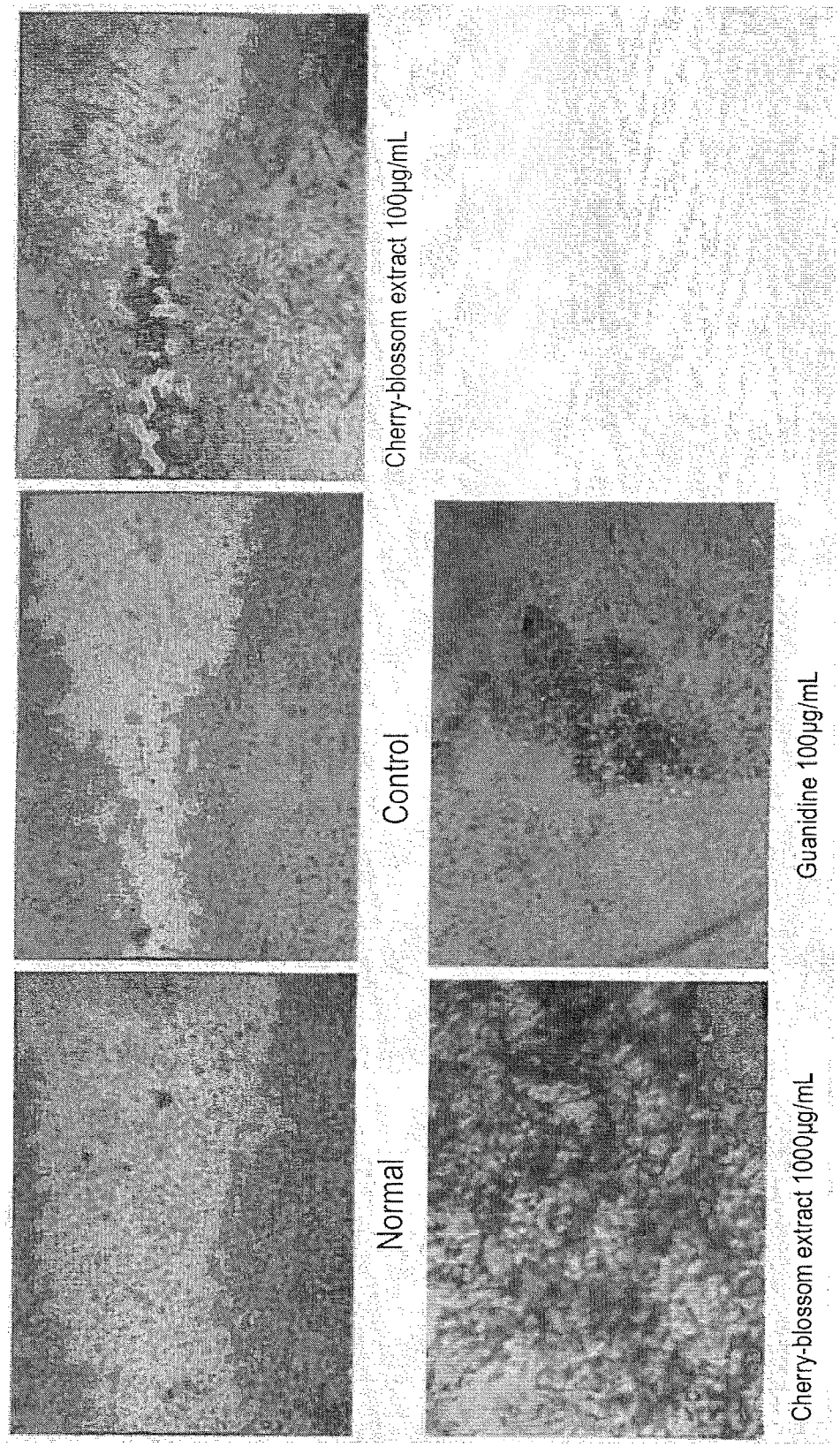
FIG. 4 shows microscopic images (×100) in 24 hours of culture according to FIG. 3.
Figure 5:
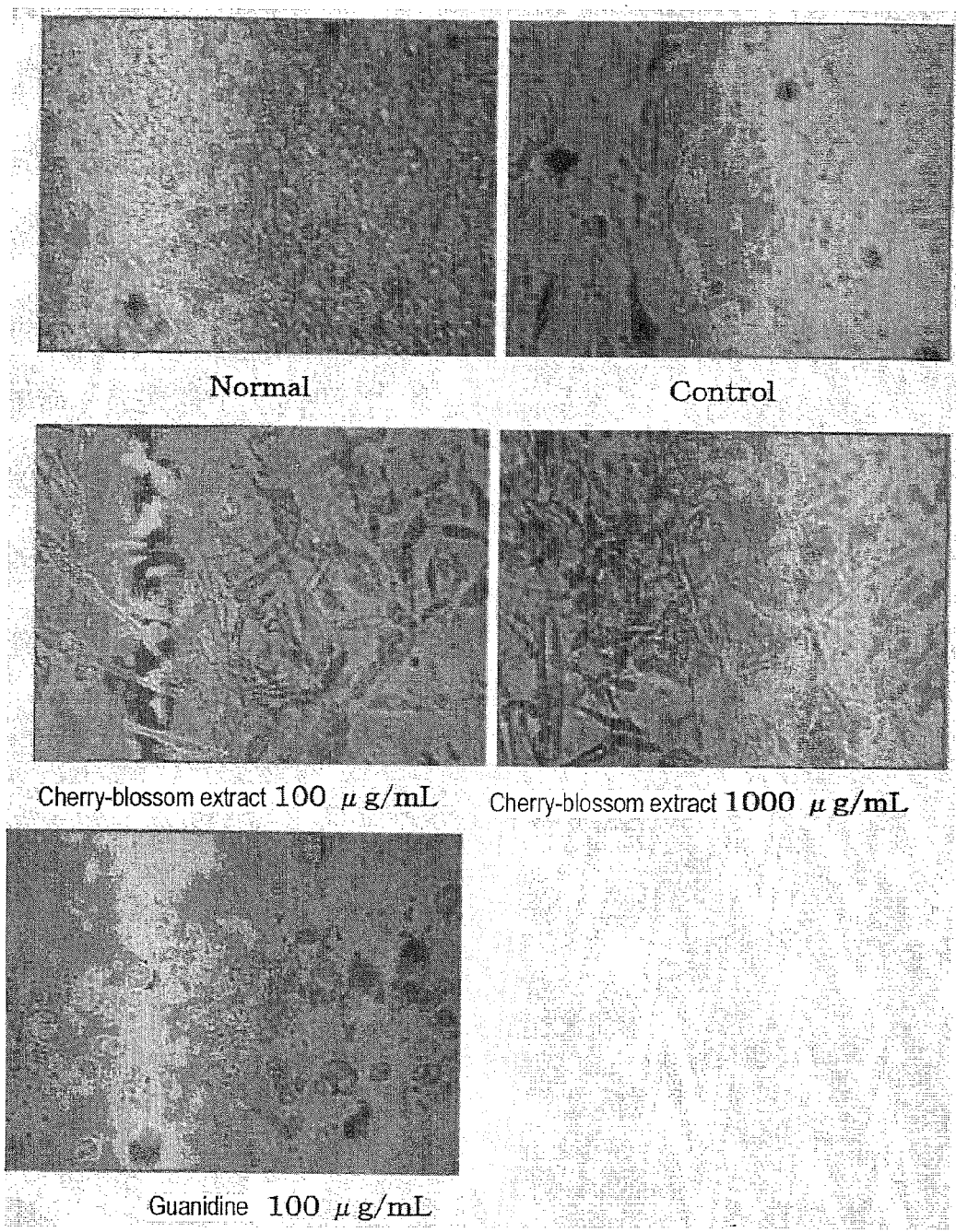
FIG. 5 shows microscopic images (×200) in 48 hours of culture according to FIG. 3.

The mixed solution of collected fibroblast ($5.4 \times 10^4$ cell) was suspended in FCS (50 μm), and collagen (450 mL) was seeded within a 24-well cell-culture plate and allowed to culture for 24 hours and 48 hours. Each culture was observed through a microscope and by the naked eye. An image observed by the naked eye is shown in FIG. 3. A microscopic image (×100), [taken] after the 24-hour culture, is shown in FIG. 4. A microscopic image (×200) [taken] after the 48-hour culture, is shown in FIG. 5. For the purpose of comparison, aminoguanidin hydrochloride which is an anti-glycation agent was also examined in the same way.

[Test 3: Result and Effects of Examples]

The result of the fibroblast and collagen solution culture, as shown in FIG. 3, is that collagen-grating formation was identified. In FIG. 3, the white hazy part shows the extension and projection of the fibroblast and collagen grating. The amount of collagen-grating formation of the Control group which was processed with glyoxal significantly decreased compared to that of Normal group. The well of fibroblast, processed with 100 and 1000 mg/mL of cherry blossom-extract (Example 1) and glyoxal showed an increase in the amount of grating formation. On the other hand, the well of fibroblast processed with 100 mg/mL of guanidine hydrochloride, compared to the control group, showed no increase in the amount of grating formation. In FIG. 4, showing the microscopic image after 24 hours of culture, it was identified that the fibroblast of the Normal group and of the Control group and of guanidine hydrochloride were spherically shaped. However, the well of 100 and 1000 mg/mL of the cherry blossom-extract (Example 1) identified the extension and projection of the fibroblast. FIG. 5, the 200-times enlarged microscopic image, after eight hours of culture, showed a few extensions of the fibroblast of the Control group. However, it was still weak compared to that of the well of 100 and 1000 mg/mL of the cherry blossom-extract (Example 1).

[Test 4: AGE Production Inhibitory Activity within the Fibroblast]

Test 4 examined the activity of the cherry blossom-extract (Example 1) and of the 1-O-(E)-Caffeoyl-β-D-glucopyranoside (Example 3) against the production of AGE (carbon methyl lysine protein) within the fibroblast (human diploid fibroblast) which was processed with glyoxal.

Figure 6:
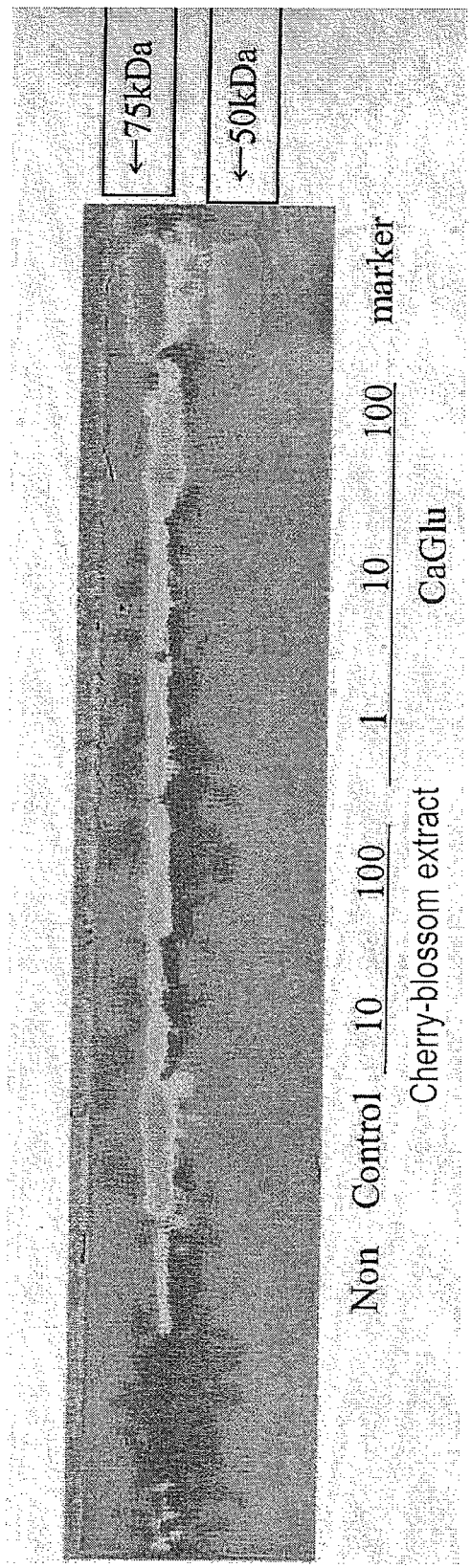
FIG. 6 shows the effect on AGE production (carboxy methyllsin protein), using Wester blotting, within the fibroblast (human diploid fibroblast) caused by glyoxal.

Human diploid fibroblast (passage number 30) was suspended in a D-MEM complete culture media, and 20 mL each was seeded within a cell culture dish of 14 cm in diameter. After 48 hours of culture, samples of various concentrations and of 40 IM of glyoxal were added to 80%-confluent cells and cultured for 5 days. After that, each sample was collected and crushed. Then, protein 10 mg was examined by the Western Blotting method using an anti-AGE antibody to detect AGE. The result as shown in FIG. 6 shows a detection of AGE by the anti-AGE antibody (HRP staining system). In FIG. 6, CaGlu means 1-O-(E)-Caffeoyl-β-D-glucopyranoside (Example 3).

[Test 4: Result and Effects of Examples]

As shown in FIG. 6, the detection of AGE using an anti-AGE antibody identified the amount of AGE that had been increased by the stimulation of glyoxal (comparison between Control and Non-control). Contrarily, the cherry blossom-extract (Example 1) of 10 mg/mL strongly inhibited the production of AGE. The effect of 100 mg/mL of the cherry-blossom extract was reduced. Yet, inhibitory activity was still found. 1-O-(E)-Caffeoyl-β-D-glucopyranoside (CaClu: Example 3) of 1 and 10 mg/mL inhibited the production of AGE. From these results, it is now clearly shown at the cellular level that cherry-blossom extract and its major substances inhibits a production of AGE.

[Test 5: AGE Production Inhibitory Activity by the Intradermal Administration of Glyoxal]

After continuously administrating the cherry-blossom extract (Example 1) in various concentrations, the AGE precursor, glyoxal, was intradermally administrated to observe its activity in the production of AGE. Based on this observation, a recommended dose of the cherry-blossom extract (Example 1) was determined.

The solution (10, 50 and 100 mg/kg) of the cherry-blossom extract (Example 1) was administered to a mouse (ICR, male, 5-week-old) once a day for 10 days. After completing the administration, glyoxal (800 mM 100 mL) was intradermally administered into the shaved back of the mouse. After 21 hours, the last administration of cherry-blossom extract (Example 1) was done to the mouse. Then, after another three hours, the mouse was immolated with an ether anesthesia, and the glyoxal-administered part was removed. The removed skin of the mouse was then crushed in 2 mL of lysis buffer (50 mM tris, 150 mM NaCl, 1% Triton X100, pH: 7.2) using Polytron Homogenizer, and the crushed material was centrifugally separated (1000×g, 7 min). Then, the supernatant was collected and refrigerated at the temperature of 20 degrees Centigrade below zero.

After measuring the protein content of the frozen supernatant by the BCA method, the AGE content was measured using an ELISA kit (Trans Genic. Inc.) for measuring glucose-derived AGEs. In addition, the AGE was detected by the Western Blotting method. The result is shown in Chart 5, as well as in FIG. 7.

[Test 5: Result and Effects of Examples]

Figure 7:
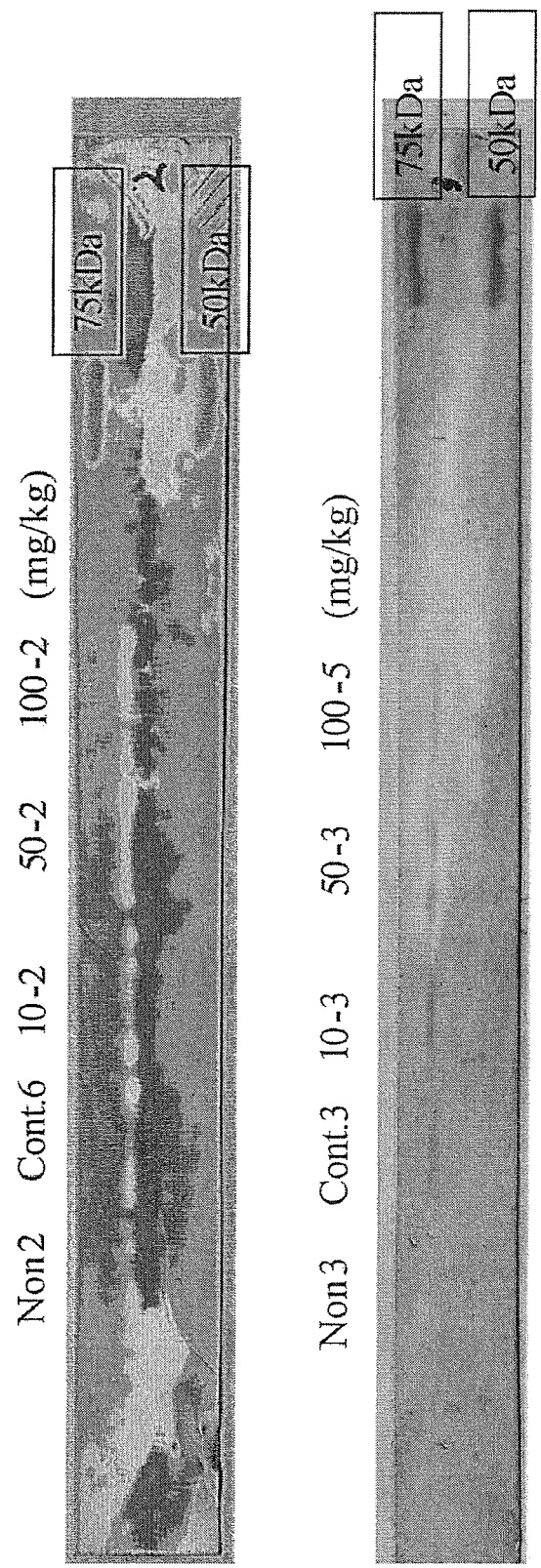
FIG. 7 shows the effect on AGE production within the glyoxal-induced skin, using Western blotting, regarding the cherry blossom extract as an example of this invention.

As shown in Chart 5 and in FIG. 7, the cherry-blossom extract (Example 1) indicated no dosage dependency. It was identified that 10 to 100 mg/kg of the cherry-blossom extract, orally administration, inhibited the production of AGE. From this result, the recommended dosage of the cherry blossom-extract (Example 1) is to be set between 10 and 100 mg/day.

CHART 5

Effect of cherry-blossom extract against intradermal AGE production caused by glyoxal (Detected by ELISA)

| | Dosage amount (mg/kg) | AGE (pg/mg protein) | Inhibition ratio (%) |
|---|---|---|---|
| Control | — | 53 ± 12 | — |
| Cherry-blossom extract | 10 | 50 ± 15 | 5.7 |
| | 50 | 18 ± 17 | 66.0 |
| | 100 | 30 ± 12 | 43.4 |

Average value ± standard error (n = 6)

[Test 6: Dermal Cell Apoptosis Inhibitory Activity by Intradermal Administration of CML-Collagen]

After the continuous administration of the cherry-blossom extract in various concentrations, the CML-collagen was intradermally administrated to observe the activity against the apoptosis of dermal cells as well as the fibroblast. The test was conducted in the following method.

Figure 8:
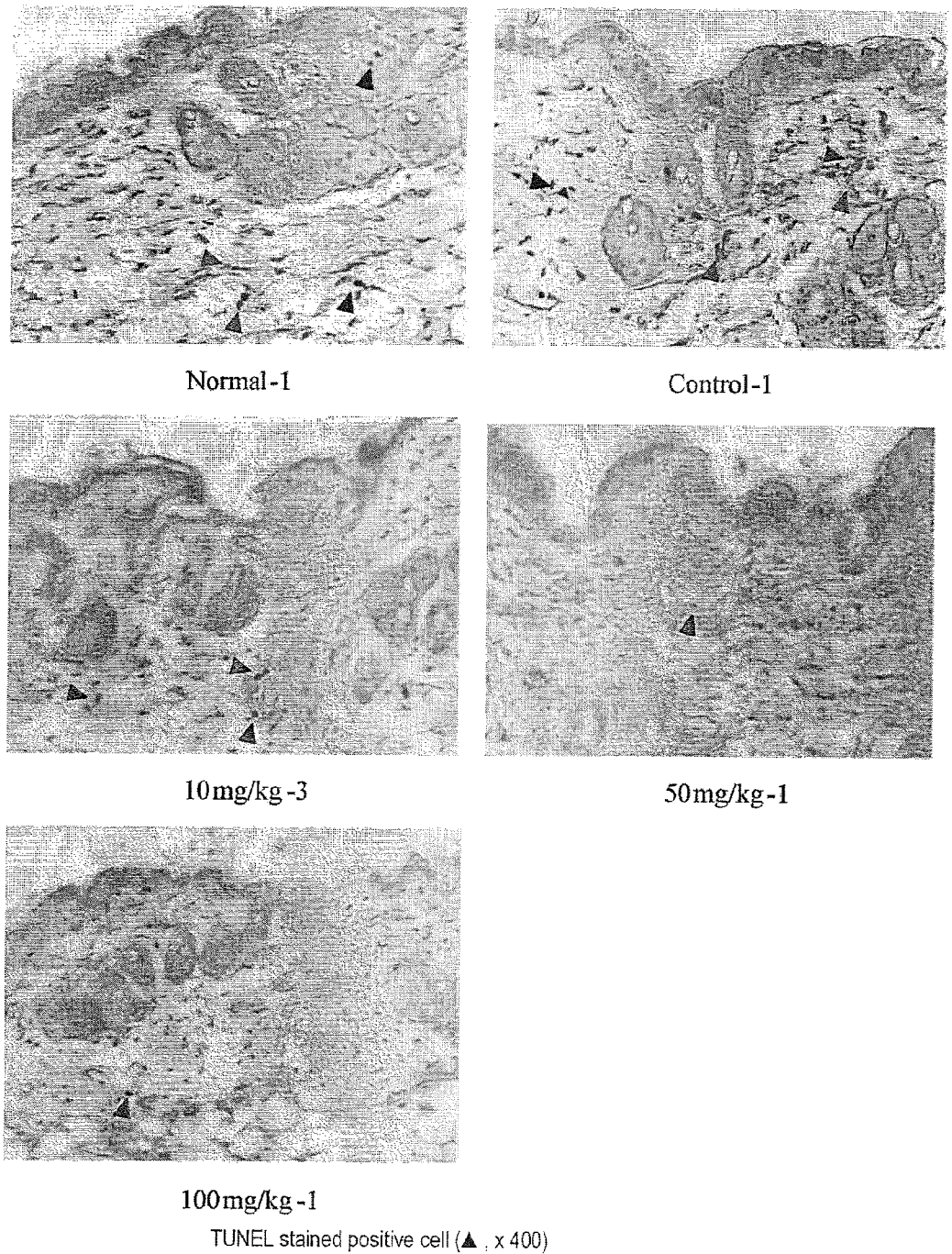
FIG. 8 shows microscopic images (×400) of TUNEL positive cells which identify the effect on dermal cell apoptosis induced by CML-collagen (Carboxymethyl lysine-collagen), regarding the cherry blossom extract as an example of this invention.

The solution (10, 50 and 100 mg/kg) of cherry-blossom extract (Example 1) was administered to a mouse (ICR, male, 5-week-old) once a day for 10 days. After completing the administration, CML-collagen (100 mg/100 mL) was intradermally administered into the shaved skin area of the mouse where the biauricular line of the occipital region of the mouse crosses a midline. Collagen was administered to the Normal group. After 21 hours, the last administration of the cherry-blossom extract (Example 1) was done to the mouse. Then, after another three hours, the mouse was immolated after being administrated an ether anesthesia. The collagen-administered part of the mouse was removed. The part removed from the mouse was immersed and fixed in a solution of 4% paraformadehyde, and the cut section was stained by TUNEL staining. To count the number of dermal cells, which were confirmed as being positive by the TUNEL staining, the image of the cross section of the skin was taken by a microscope (×400) and processed with color gradations from purple to orange to identify the number of cells. To calculate the area of the inner skin, a printed image of the cross section of the inner skin was measured by a digital planimeter, and the scale was multiplied. The result is shown in Chart 6, as well as in FIG. 8. In FIG. 8, the part marked with a ▲ means TUNEL-positive cells.

[Test: Result and Effects of Examples]

By the administration of CML-collagen, the number of TUNEL-positive cells in the inner skin increased. To the contrary, the cherry-blossom extract (Example 1) decreased the number of TUNEL-positive cells in a dosage-dependent manner. From this result, it was identified that the cherry-blossom extract (Example 1) inhibited fibroblast apoptosis of the skin caused by the CML-collagen, in vivo.

CHART 6

Effect of cherry-blossom extract against dermal cell apoptosis caused by CML-collagen

|  | Dosage amount (mg/kg) | Number of TUNEL stained positive cells (cells/mm$^2$) | Inhibition ratio (%) |
|---|---|---|---|
| Normal | — | 27.2 ± 1.7 | — |
| Control | — | 36.4 ± 10.6 | — |
| Cherry-blossom extract | 10 | 22.7 ± 5.4 | 149 |
|  | 50 | 14.5 ± 2.9 | 238 |
|  | 100 | 8.8 ± 1.7* | 300 |

Average value ± standard error (n = 3)

* $p < 0.05$

The following charts present examples of the compounds using cherry-blossom extract (Example 1) as an AGE production inhibitor, or the like. However the compounds shown below are not limited to just these.

CHART 7

Blending example 1: Chewing gums

| | |
|---|---|
| Sugar | 53.0 wt % |
| Gum base | 20.0 |
| Glucose | 10.0 |
| Starch syrup | 16.0 |
| Aroma chemical | 0.5 |
| AGE production inhibitor, etc | 0.5 |
| | 100.0 wt % |

CHART 8

Blending example 2: Gummies

| | |
|---|---|
| Reduction sugar | 40.0 wt % |
| Granulated sugar | 20.0 |
| Glucose | 20.0 |
| Gelatine | 4.7 |
| Water | 9.68 |
| Yuzu juice (Citrus junos) | 4.0 |
| Yuzu flavor | 0.6 |
| Pigment | 0.5 |
| AGE production inhibitor, etc | 0.5 |
| | 100.0 wt % |

CHART 9

Blending example 3: Candies

| | |
|---|---|
| Sugar | 50.0 wt % |
| Starch syrup | 33.0 |
| Water | 14.4 |
| Organic acid | 2.0 |
| Aroma chemical | 0.2 |
| AGE production inhibitor, etc | 0.4 |
| | 100.0 wt % |

CHART 10

Blending example 4: Yogurt (Hard type/Soft type)

| | |
|---|---|
| Milk | 41.5 wt % |
| Powdered skim milk | 5.8 |
| Sugar | 8.0 |
| Agar-agar | 0.15 |
| Gelatine | 0.1 |
| Lactic acid bacterium | 0.005 |
| AGE production inhibitor, etc | 0.4 |
| Aroma chemical | Minute amount |
| Water | Rest |
| | 100.0 wt % |

CHART 11

Blending example 5: Soft drinks

| | |
|---|---|
| Fructose glucose solution | 30.0 wt % |
| Emulsifying agent | 0.5 |
| AGE production inhibitor, etc | 0.3 |
| Aroma chemical | Appropriate amount |
| Distilled water | Rest |
| | 100.0 wt % |

CHART 12

Blending example 6: Tablet-shaped sweets

| | |
|---|---|
| Sugar | 76.4 wt % |
| Glucose | 19.0 |
| Glycerine fatty acid ester | 0.2 |
| AGE production inhibitor, etc | 0.5 |
| Distilled water | 3.9 |
| | 100.0 wt % |

CHART 13

Blending example 7: Soft capsules

| | |
|---|---|
| Brown rice germ oil | 47.0 wt % |
| Yuzu (Citrus junos) seed oil | 40.0 |
| Emulsifying agent | 12.0 |
| AGE production inhibitor, etc | 1.0 |
| | 100.0 wt % |

CHART 14

Blending example 8: Tablets

| | |
|---|---|
| Lactose | 54.0 wt % |
| Crystaline Cellulose | 30.0 |
| Starch splitting product | 10.0 |
| Glycerin fatty acid ester | 5.0 |
| AGE production inhibitor, etc | 1.0 |
| | 100.0 wt % |

CHART 15

Blending example 8: Tablets

| | |
|---|---|
| Lactose | 54.0 wt % |
| Crystaline Cellulose | 30.0 |
| Starch splitting product | 10.0 |

CHART 15-continued

Blending example 8: Tablets

| | | |
|---|---|---|
| | Glycerin fatty acid ester | 5.0 |
| | AGE production inhibitor, etc | 1.0 |
| | | 100.0 wt % |

CHART 16

Blending example 10: Skin lotions

| | | |
|---|---|---|
| | Ethanol | 5.0 wt % |
| | Glycerin | 2.0 |
| | 1,3-butylene glycol | 2.0 |
| | Polyethylene oleyl ether | 0.5 |
| | Sodium citrate | 0.1 |
| | Citric acid | 0.1 |
| | AGE production inhibitor, etc | 0.1 |
| | Distilled water | Rest |
| | | 100.0 wt % |

CHART 17

Blending example 11: Body gels

| | | |
|---|---|---|
| | Macadamia nut oil | 2.0 wt % |
| | Octyl decyl myristate | 10.0 |
| | Methylphenyl polysiloxane | 5.0 |
| | Behenyl alcohol | 3.0 |
| | Stearic acid | 3.0 |
| | Bathyl alcohol | 1.0 |
| | Glycel monostearate | 1.0 |
| | Tetra oleic acid polyoxyethylene sorbit | 2.0 |
| | Hydrogenated soybean phosphatide | 1.0 |
| | Ceramide | 0.1 |
| | Retinol palmitate | 0.1 |
| | Preservative agent | Appropriate amount |
| | Centella asiatica extract | 1.0 |
| | AGE production inhibitor, etc | 1.0 |
| | 1,3-butylene glycol | 5.0 |
| | Distilled water | Rest |
| | | 100.0 wt % |

CHART 18

Blending example 12: Cosmetic emulsion

| | | |
|---|---|---|
| | Squalene | 4.0 wt % |
| | Vaseline | 2.5 |
| | Cetanol | 2.0 |
| | Glycerin | 2.0 |
| | Oleophilic glycerine monostearate | 1.0 |
| | Stearic acid | 1.0 |
| | L-arginine | 1.0 |
| | AGE production inhibitor | 0.5 |
| | Potassium hydroxide | 0.1 |
| | Aroma chemical | Minute amount |
| | Distilled water | Rest |
| | | 100.0 wt % |

CHART 19

Blending example 13: Bath agent (liquid type)

| | | |
|---|---|---|
| | Propylene glycol | 50.0 wt % |
| | Ethanol | 20.0 |

CHART 19-continued

Blending example 13: Bath agent (liquid type)

| | | |
|---|---|---|
| | Sodium sulphate | 5.0 |
| | AGE production inhibitor | 0.5 |
| | Lanoline | 0.5 |
| | Avocado oil agent | 0.5 |
| | Pigment | 1.5 |
| | Aroma chemical | 22.0 |
| | | 100.0 wt % |

Compounds 1 to 13, above, contain the cherry-blossom extract (Example 1). Yet, they still may contain cherry-leaf extract (Example 2) or any one of Examples 3 to 9: 1-O-(E)-Caffeoyl-β-D-glucopyranoside, 1-O-(E)-Coumaroyl-β-D-Glucopyranoside and, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside and Quercetin 3-O-(6"-malony)-β-D-Glucopyranoside. It is also possible to use a mixture of the above seven substances (Examples 3 to 9).

INDUSTRIAL APPLICABILITY

As described above, this invention makes it possible to inhibit the production of AGE and to prevent cells and intercellular matrix from suffering damage induced by AGE. From this result, this invention also makes it possible to effectively prevent and cure diabetes and diabetic complications, thus effectively preventing the skin from aging.

The invention claimed is:

1. A method of inhibiting advanced glycation end product production in a person comprising the step of administering an effective amount of a cherry blossom or cherry leaf extract comprising each of 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and Quercetin 3-O-(6"-malony)-β-D-glucopyranoside to the person for inhibiting of advanced glycation end product production,
    wherein the cherry blossom or cherry leaf extract is made according to the following steps:
    (a) extracting the cherry blossom or cherry leaf extract with 20 to 50 wt % hydrous ethanol,
    (b) absorbing the extract obtained in step (a) by an absorbent, comprising porous reverse phase resin, eluting the extract in water and removing the aqueous eluted extract, thereby leaving an eluted extract, and
    (c) after step (b), further eluting the eluted extract with a C1 to C5 alcohol, and then concentrating the further eluted extract.

2. The method of claim 1, wherein an agent is administered to the person, the agent including the cherry blossom or cherry leaf extract as an active substance of the agent.

3. A method of inhibiting fibroblast apoptosis in a person comprising the step of administering an effective amount of a cherry blossom or cherry leaf extract comprising each of 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and Quercetin 3-O-(6"-malony)-β-D-glucopyranoside to the person for inhibiting fibroblast apoptosis, wherein the cherry blossom or cherry leaf extract is made according to the following steps:
(a) extracting cherry blossom or cherry leaf extract with 20 to 50 wt % hydrous ethanol,
(b) absorbing the extract obtained in step (a) by an absorbent, comprising porous reverse phase resin, eluting the extract in water and removing the aqueous eluted extract, thereby leaving an eluted extract, and
(c) after step (b), further eluting the eluted extract with a C1 to C5 alcohol, and then concentrating the further eluted extract.

4. The method of claim 3, wherein an agent is administered to the person, the agent including the cherry blossom or cherry leaf extract as an active substance of the agent.

5. A method of promoting of human fibroblast-collagen grating formulation in a person comprising the step of administering an effective amount of a cherry blossom extract comprising each of 1-O-(E)-Caffeoyl-β-D-glucopyranoside, 1-O-(E)-Coumaroyl-β-D-glucopyranoside, 1-O-(E)-Cinnamoyl-β-D-glucopyranoside, Kaempferol 3-O-β-D-glucopyranoside, Quercetin 3-O-β-D-glucopyranoside, Kaempferol 3-O-(6"-malony)-β-D-glucopyranoside, and Quercetin 3-O-(6"-malony)-β-D-glucopyranoside to the person for promoting of human fibroblast-collagen grating formulation,
wherein the cherry blossom or cherry leaf extract is made according to the following steps:
(a) extracting cherry blossom or cherry leaf extract with 20 to 50 wt % hydrous ethanol,
(b) absorbing the extract obtained in step (a) by an absorbent, comprising porous reverse phase resin, eluting the extract in water and removing the aqueous eluted extract, thereby leaving an eluted extract, and
(c) after step (b), further eluting the eluted extract with a C1 to C5 alcohol, and then concentrating the further eluted extract.

6. The method of claim 5, wherein an agent is administered to the person, the agent including the cherry blossom or cherry leaf extract as an active substance of the agent.

* * * * *